United States Patent
Nielsen et al.

(10) Patent No.: US 6,836,683 B2
(45) Date of Patent: Dec. 28, 2004

(54) IMPLANTABLE MEDICAL DEVICE HAVING FLAT ELECTROLYTIC CAPACITOR FABRICATED WITH EXPANSION RIVETED ANODE SHEETS

(75) Inventors: Christian S. Nielsen, River Falls, WI (US); Timothy T. Bomstad, Inver Grove Heights, MN (US)

(73) Assignee: Medtronic, Inc., Minneapolis, MN (US)

(*) Notice: Subject to any disclaimer, the term of this patent is extended or adjusted under 35 U.S.C. 154(b) by 450 days.

(21) Appl. No.: 10/124,508

(22) Filed: Apr. 18, 2002

(65) Prior Publication Data

US 2003/0199942 A1 Oct. 23, 2003

(51) Int. Cl.$^7$ .............................................. A61N 1/362
(52) U.S. Cl. ...................................................... 607/36
(58) Field of Search .............................. 607/5, 36, 37; 361/500, 508–512; 29/25.03; 228/107

(56) References Cited

U.S. PATENT DOCUMENTS

| | | | |
|---|---|---|---|
| 4,254,775 A | 3/1981 | Langer ................... 128/419 D |
| 4,635,840 A | * 1/1987 | Cenanovic ................... 228/107 |
| 4,942,501 A | 7/1990 | MacFarlane et al. ......... 361/523 |
| 5,086,374 A | 2/1992 | MacFarlane et al. ......... 361/525 |
| 5,131,388 A | 7/1992 | Pless et al. ............. 128/419 D |
| 5,146,391 A | 9/1992 | MacFarlane et al. ......... 361/525 |
| 5,153,820 A | 10/1992 | MacFarlane et al. ......... 361/525 |
| 5,522,851 A | 6/1996 | Fayram ........................... 607/5 |
| 5,584,890 A | 12/1996 | MacFarlane et al. ....... 29/25.03 |
| 5,628,801 A | 5/1997 | MacFarlane et al. ....... 29/25.03 |
| 5,748,439 A | 5/1998 | MacFarlane et al. ......... 361/525 |
| 6,006,133 A | 12/1999 | Lessar et al. .................. 607/5 |
| 6,321,114 B1 | 11/2001 | Nutzman et al. |

FOREIGN PATENT DOCUMENTS

| | | |
|---|---|---|
| EP | 0743662 | 11/1996 |
| WO | WO 0202186 | 10/2002 |

OTHER PUBLICATIONS

"Implantable Cardioveters and Defibrillators," *Current Problems in Cardiology*, vol. XIV, No. 12, Dec. 1989, Year Book Medical Publishers, Chicago.

"High Energy Density Capactors for Implantable Defibrillators," presented by P. Lunsmann and D. MacFarlane at CARTS 96: 16$^{th}$ Capacitor and Resistor Technology Symposium, Mar. 11–15 1996, and at CARTS–EUROPE 96: 10$^{th}$ European Passive Components Symposium, Oct. 7–11, 1996, pp. 35–39.

* cited by examiner

Primary Examiner—George Manuel
(74) Attorney, Agent, or Firm—Girma Wolde-Michael; Daniel G. Chapik

(57) ABSTRACT

Implantable medical devices (IMDs) and their various components, including flat electrolytic capacitors for same, and methods of making and using same, particularly an improved electrolytic capacitor fabricated of an electrode stack assembly comprising a plurality of capacitor layers stacked in registration upon one another. Each capacitor layer comprises a cathode layer having a cathode tab, an anode layer having an anode tab, and a separator layer located between adjacent anode and cathode layers. The anode layer is fabricated of side-by-side stacked anode sheets joined together by at least one malleable member that is fitted into substantially aligned anode sheet bores extending through each sheet and expanded therein to bear against the valve metal core layer of the anode sheets exposed by the bores to effect electrical and mechanical connection of the anode sheets and the anode tab.

40 Claims, 15 Drawing Sheets

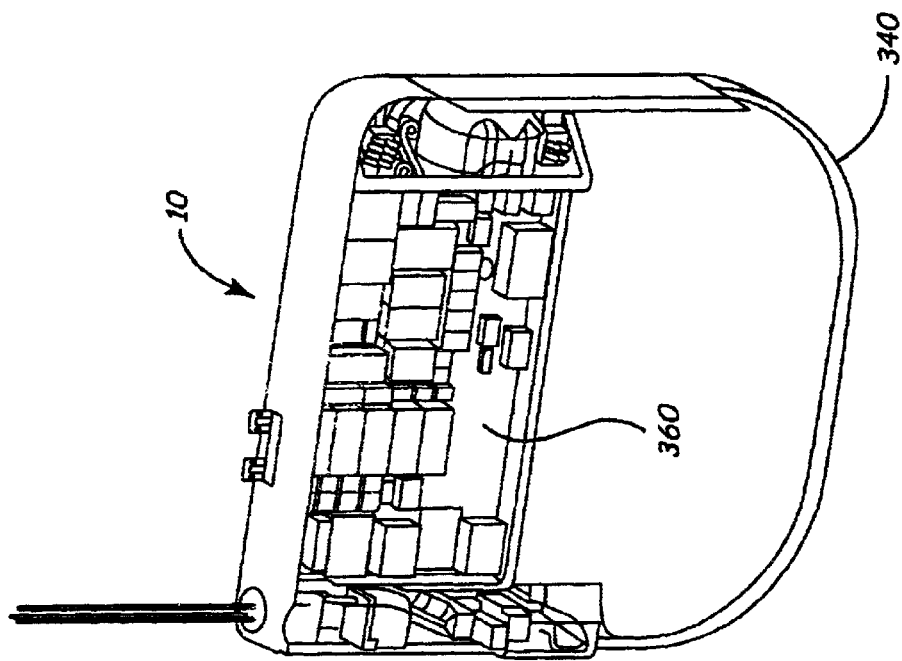
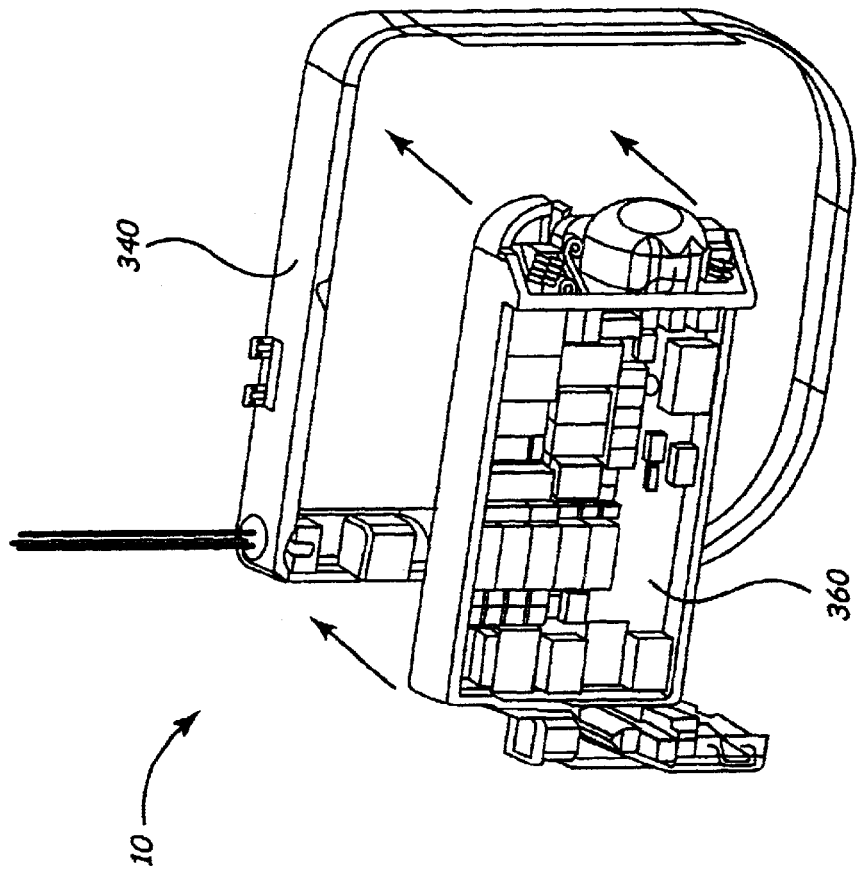

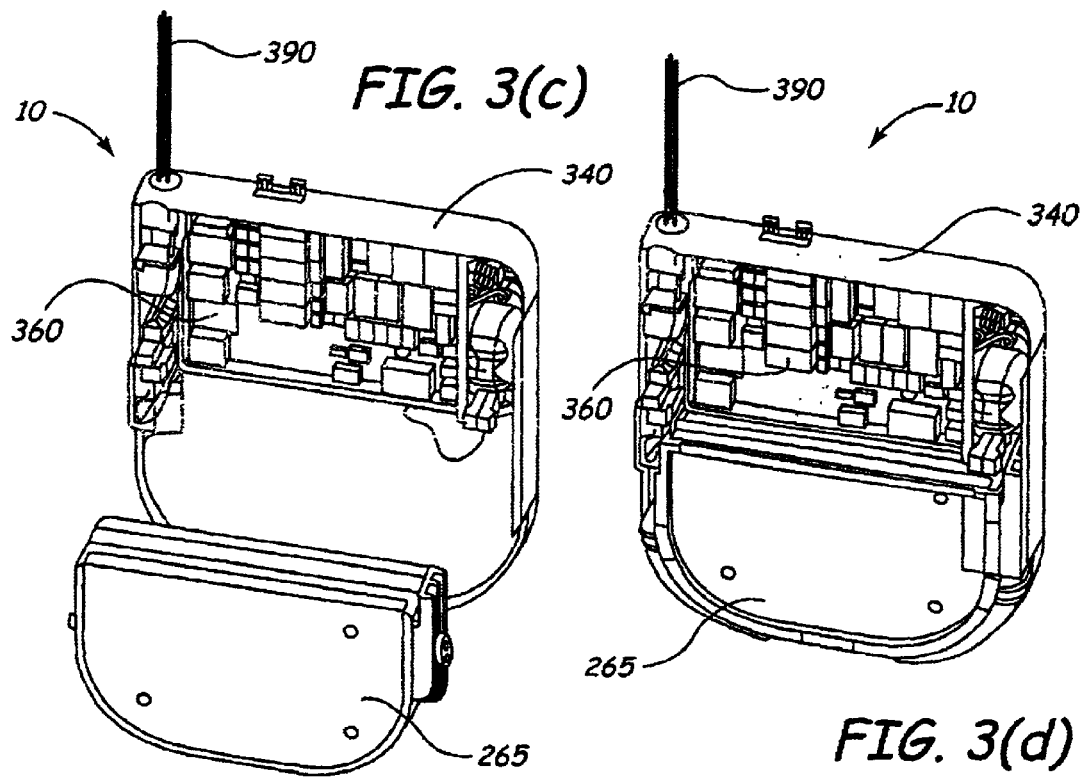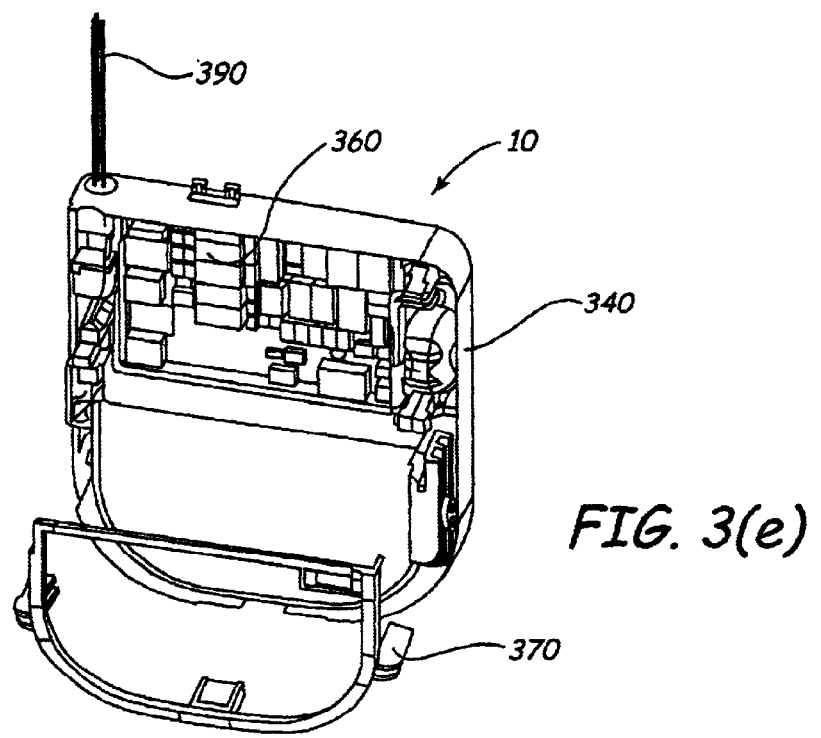

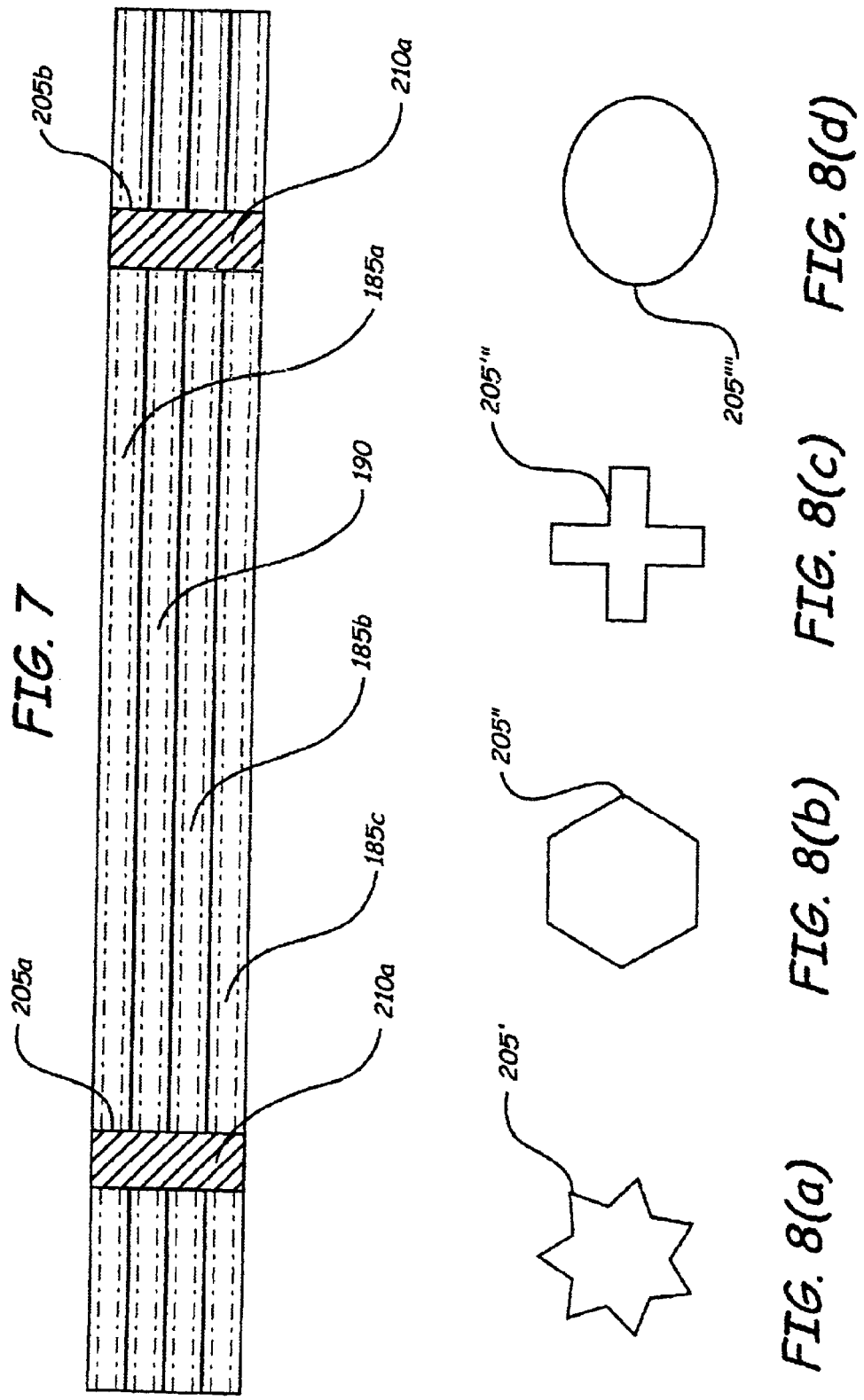

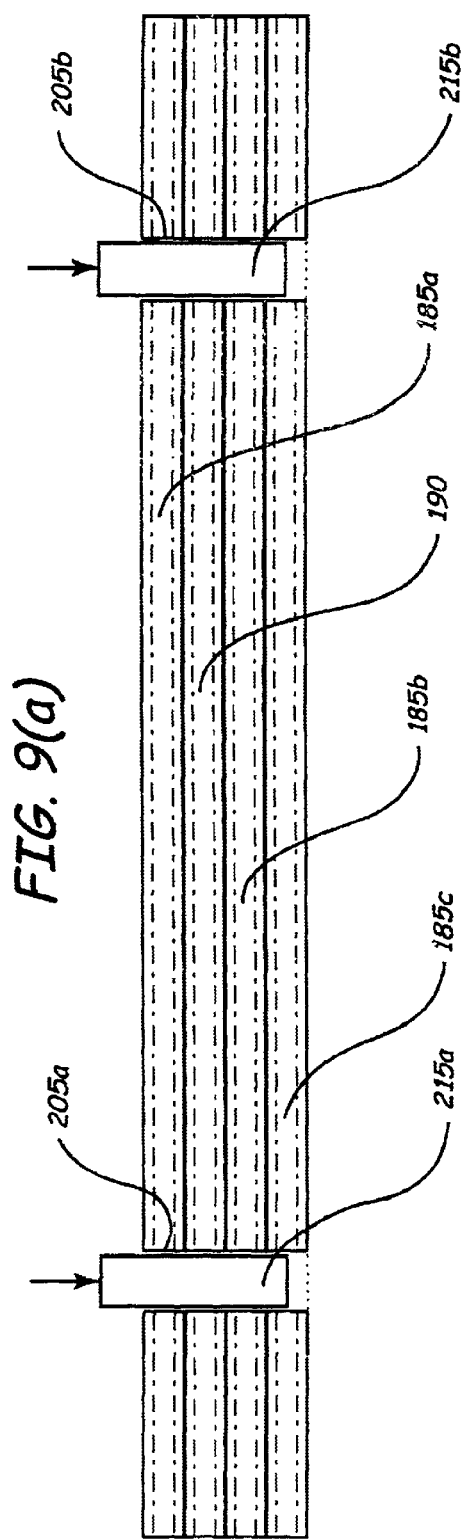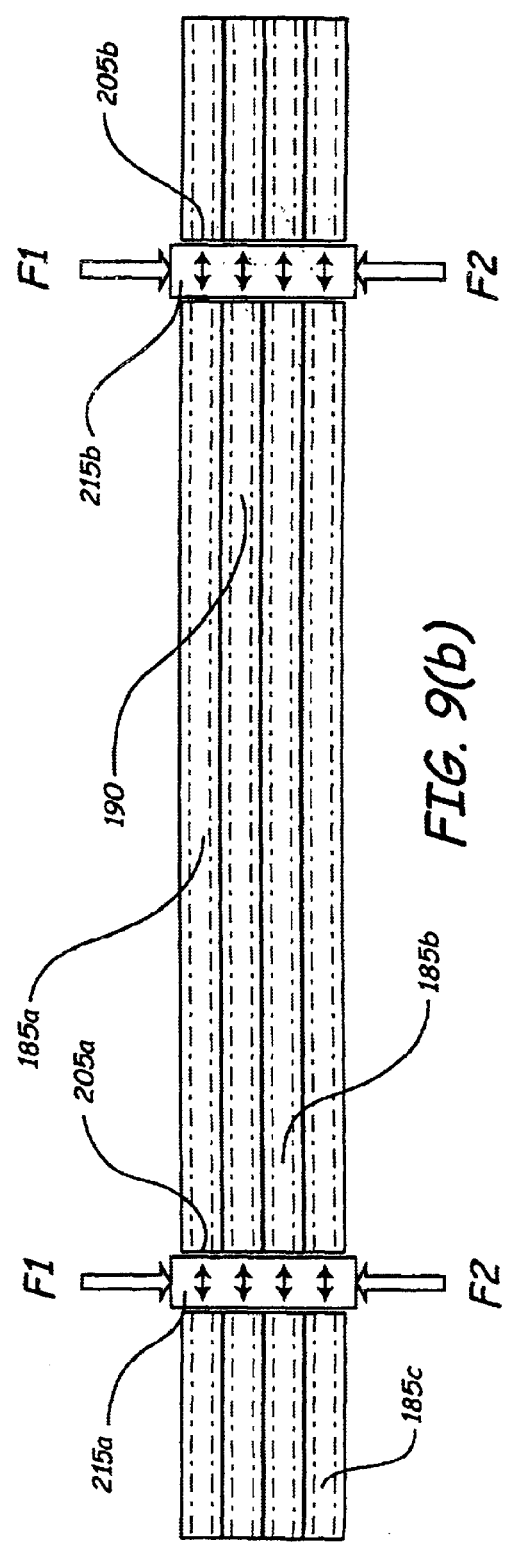

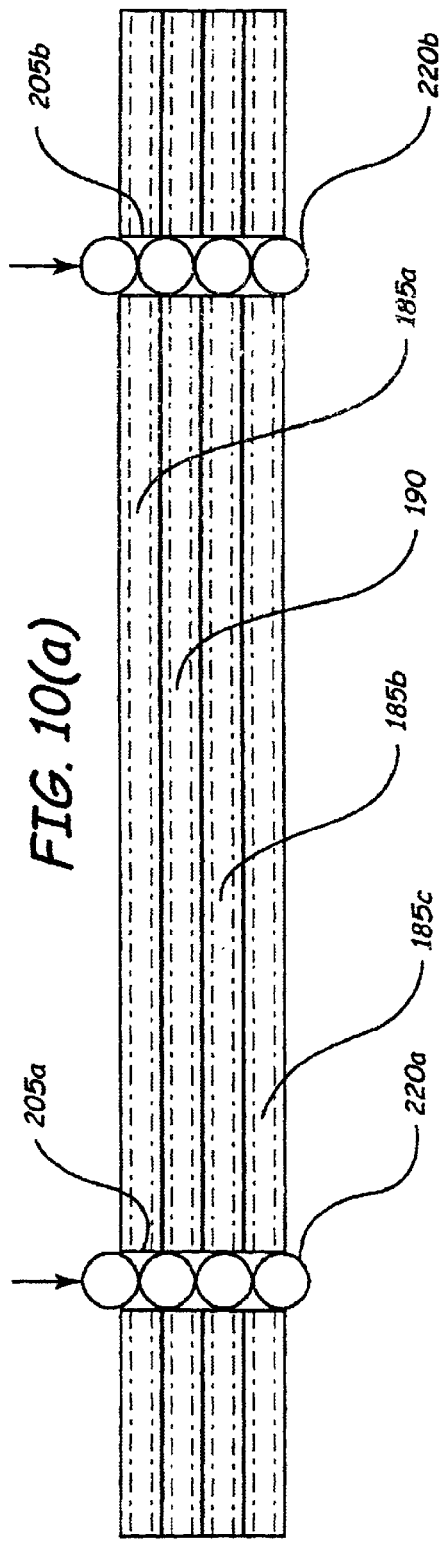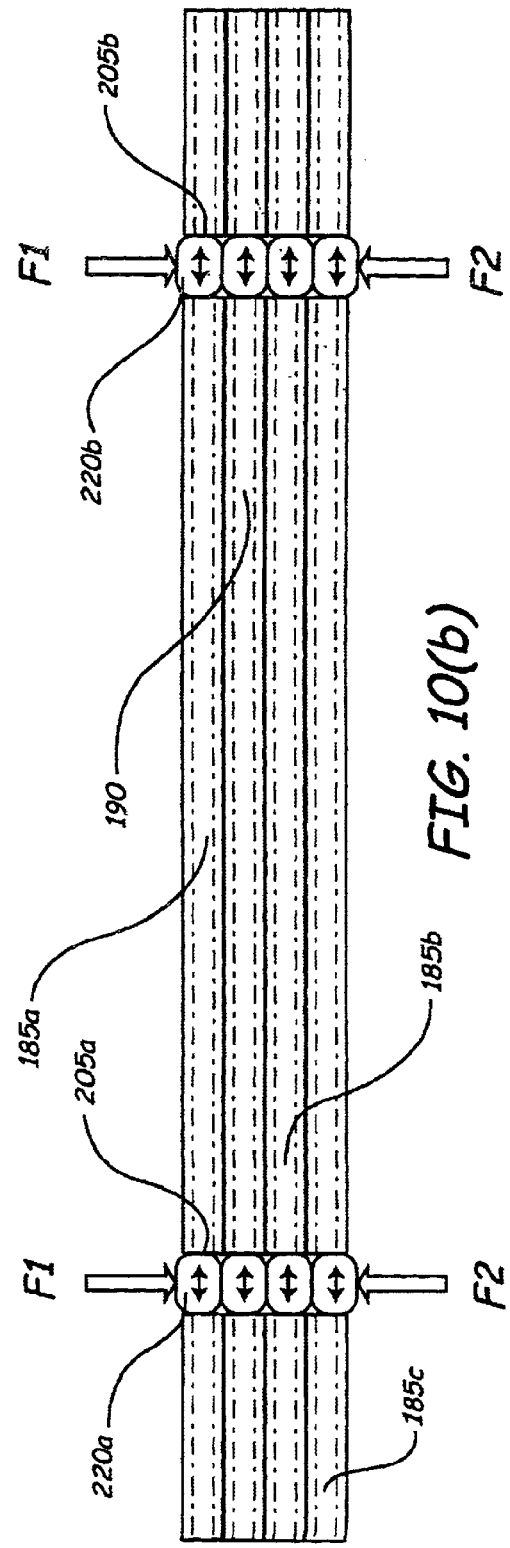

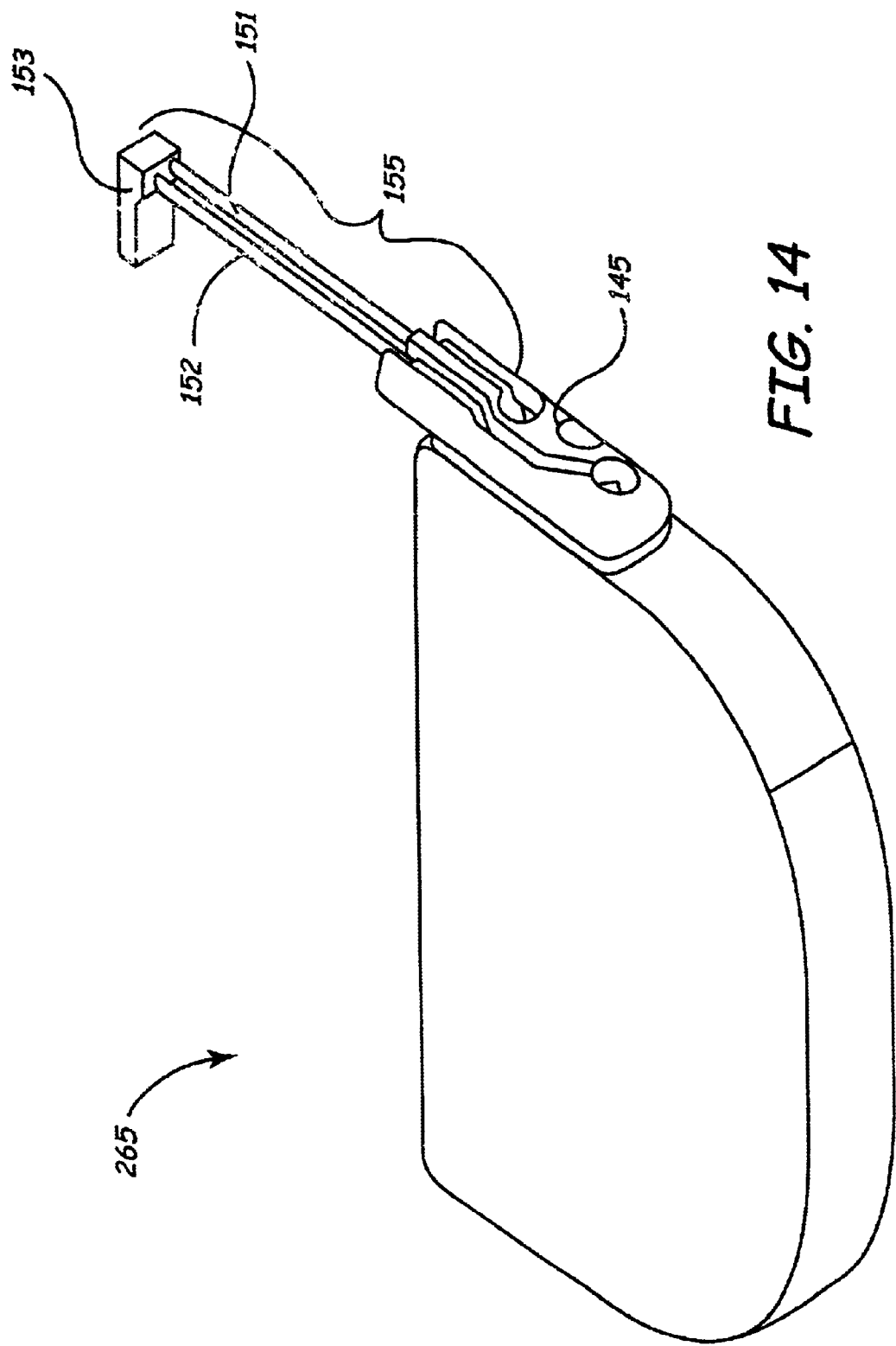

IMPLANTABLE MEDICAL DEVICE HAVING FLAT ELECTROLYTIC CAPACITOR FABRICATED WITH EXPANSION RIVETED ANODE SHEETS

FIELD OF THE INVENTION

This invention relates to implantable medical devices (IMDs) and their various components, including flat electrolytic capacitors for same, and methods of making same, particularly such capacitors fabricated of a plurality of stacked capacitor layers each having anode layers fabricated of a plurality of anodized valve metal anode sheets.

BACKGROUND OF THE INVENTION

A wide variety of IMDs are known in the art. Of particular interest are implantable cardioverter-defibrillators (ICDs) that deliver relatively high-energy cardioversion and/or defibrillation shocks to a patient's heart when a malignant tachyarrhythmia, e.g., atrial or ventricular fibrillation, is detected. The shocks are developed by discharge of one or more high voltage electrolytic capacitor that is charged up from an ICD battery. Current ICDs typically possess single or dual chamber pacing capabilities for treating specified chronic or episodic atrial and/or ventricular bradycardia and tachycardia and were referred to previously as pacemaker/cardioverter/defibrillators (PCDs). Earlier developed automatic implantable defibrillators (AIDs) did not have cardioversion or pacing capabilities. For purposes of the present invention ICDs are understood to encompass all such IMDs having at least high voltage cardioversion and/or defibrillation capabilities.

Energy, volume, thickness and mass are critical features in the design of ICD implantable pulse generators (IPGs) that are coupled to the ICD leads. The battery(s) and high voltage capacitor(s) used to provide and accumulate the energy required for the cardioversion/defibrillation shocks have historically been relatively bulky and expensive. Presently, ICD IPGs typically have a volume of about 40 to about 60 cc, a thickness of about 13 mm to about 16 mm and a mass of approximately 100 grams.

It is desirable to reduce the volume, thickness and mass of such capacitors and ICD IPGs without reducing deliverable energy. Doing so is beneficial to patient comfort and minimizes complications due to erosion of tissue around the ICD IPG. The high voltage capacitor(s) are among the largest components that must be enclosed within the ICD IPG housing. Reductions in size of the capacitors may also allow for the balanced addition of volume to the battery, thereby increasing longevity of the ICD IPG, or balanced addition of new components, thereby adding functionality to the ICD IPG. It is also desirable to provide such ICD IPGs at low cost while retaining the highest level of performance. At the same time, reliability of the capacitors cannot be compromised.

Various types of flat and spiral-wound capacitors are known in the art, some examples of which are described as follows and/or may be found in the patents listed in Table 1 of commonly assigned U.S. Pat. No. 6,006,133. Typically, an electrolytic capacitor is fabricated with a capacitor case enclosing a "valve metal" (e.g., aluminum) anode layer (or "electrode"), a valve metal (e.g. aluminum) cathode layer (or "electrode"), and a Kraft paper or fabric gauze spacer or separator impregnated with a solvent based liquid electrolyte interposed therebetween. The aluminum anode layer is typically fabricated from aluminium foil that is first etched and then "formed" by passage of electrical current through the anode layer to oxidize the etched surfaces so that the aluminium oxide functions as a dielectric layer. The electrolyte comprises an ion producing salt that is dissolved in a solvent and provides ionic electrical conductivity between the cathode layer and the aluminum oxide dielectric layer. The energy of the capacitor is stored In the electromagnetic field generated by opposing electrical charges separated by the aluminum oxide layer disposed on the surface of the anode layer and is proportional to the surface area of the etched aluminum anode layer. Thus, to minimize the overall volume of the capacitor one must maximize anode surface area per unit volume without increasing the capacitor's overall (i.e., external) dimensions. The separator material, anode and cathode layer terminals, internal packaging, electrical interconnections, and alignment features and cathode material further increase the thickness and volume of a capacitor. Consequently, these and other components in a capacitor and the desired capacitance limit the extent to which its physical dimensions may be reduced.

Some ICD IPGs employ commercial photoflash capacitors similar to those described by Troup in "Implantable Cardioverters and Defibrillators," *Current Problems in Cardiology*, Volume XIV, Number 12, Dec. 1989, Year Book Medical Publishers, Chicago, and as described in U.S. Pat. No. 4,254,775. The electrodes or anode and cathodes are wound into anode and cathode layers separated by separator layers of the spiral. Most commercial photoflash capacitors contain a core of separator paper intended to prevent brittle, highly etched aluminum anode foils from fracturing during winding of the anode, cathode, and separator layers into a coiled configuration. The cylindrical shape and paper core of commercial photoflash capacitors limits the volumetric packaging efficiency and thickness of an ICD IPG housing made using same.

More recently developed ICD IPGs employ one or more flat or "prismatic", high voltage, electrolytic capacitor to overcome some of the packaging and volume disadvantages associated with cylindrical photoflash capacitors. Flat aluminum electrolytic capacitors for use in ICD IPGs have been disclosed, e.g., those Improvements described in "High Energy Density Capacitors for Implantable Defibrillators" presented by P. Lunsmann and D. MacFarlane at *CARTS 96: 16th Capacitor and Resistor Technology Symposium*, 11–15 Mar. 1996, and at *CARTS-EUROPE 96: 10th European Passive Components Symposium.*, 7–11 Oct. 1996, pp. 35–39. Further features of flat electrolytic capacitors for use in ICD IPGs are disclosed in U.S. Pat. Nos. 4,942,501; 5,086,374; 5,131,388; 5,146,391; 5,153,820; 5,522,851, 5,562,801; 5,628,801; and 5,748,439, all issued to MacFarlane et al.

For example, U.S. Pat. Nos. 5,131,388 and 5,522,851 disclose a flat capacitor having a plurality of stacked capacitor layers each comprising an "electrode stack subassembly". Each capacitor layer contains one or more anode sheet forming an anode layer having an anode tab, a cathode sheet or layer having a cathode tab and a separator for separating the anode layer from the cathode layer.

Electrical performance of such electrolytic capacitors is affected by the surface area of the anode and cathode layers and also by the resistance associated with the electrolytic capacitor itself, called the equivalent series resistance (ESR). The ESR is a "hypothetical" series resistance that represents all energy losses of an electrolytic capacitor regardless of source. The ESR results in a longer charge time (or larger build factor) and lower discharge efficiency. Therefore, it is desirable to reduce the ESR to a minimum.

Typically, ESR is minimized by fabricating the anode layer of each capacitor layer from highly etched valve metal foil, e.g., aluminum foil, that has a microscopically contoured, etched surface with a high concentration of pores extending part way through the anode foil along with tunnels extending all the way through the anode foil (through-etched or tunnel-etched) or only with a high concentration of pores extending part way through the anode foil (nonthrough-etched). In either case, such a through-etched or nonthrough-etched anode sheet cut from such highly etched foil exhibit a total surface area much greater than its nominal (length times width) surface area. A surface area coefficient, the ratio of the microscopic true surface area to the macroscopic nominal area, may be as high as 100:1, which advantageously increases capacitance. Through-etched or tunnel-etched anode sheets exhibit a somewhat lower ratio due to the absence of a web or barrier surface closing the tunnel as in nonthrough-etched anode sheets.

After the aluminum foil is etched, the aluminum oxide layer on the etched surface is "formed" by applying voltage to the foil through an electrolyte such as boric acid or citric acid and water or other solutions familiar to those skilled in the state of the art. Typically, individual anode sheets are punched, stamped or otherwise cut out of the foil in a shape to conform to the capacitor package following formation of the aluminum oxide on the foil. The cut edges around the periphery of the anode sheets are carefully cleaned to remove particulates of anode material that can get caught between the capacitor layers in the electrode stack assembly resulting in a high leakage current or capacitor failure. Anode layers either comprise a single anode sheet or multiple anode sheets. Stacking the anode layer, s separator layers, and cathode layer together assembles capacitor layers, and electrode stack assemblies are assembled by stacking a plurality of capacitor layers together, separated by separator layers. The cut edges of the anode and cathode layers and any other exposed aluminum are then reformed in the capacitor during the aging process to reduce leakage current.

In order to increase capacitance (and energy density), multiple anode sheets are stacked together to form the multiple sheet anode layer as described above. Through-etched or tunnel-etched anode sheets need to be used In such multiple sheet anode layers to ensure that electrolyte is distributed over all of the aluminum oxide layers of the sandwiched inner anode sheets and to provide a path for ionic communication. But, then the gain in surface area is not as high as that which can be achieved with a like number of stacked non-through-etched anode sheets that have a remaining solid section in their center.

For example, the '890 patent discloses the use of an anode layer fabricated from a highly etched center sheet with a solid core and two tunnel-etched anode sheets sandwiching the center sheet. This arrangement is intended to allow the electrolyte, and thus the conducting ions, to reach all surface areas of the three-sheet anode layer while preventing the ions from passing all the way through the anode layer. More than three tunnel etched anode sheets can be used in the anode layer depending on the desired electrical performance.

The aluminum oxide layers electrically Isolate the aluminum sheets of the aluminum layer from each other, and an electrical connection must be made between the underlying aluminum valve metal of each anode sheet of the anode layer. In one approach, each anode sheet of each anode layer is fabricated with an outwardly projecting anode tab. The tabs of the anode layers and the cathode layers of all of the capacitor layers of the stack are electrically connected in parallel to form a single capacitor or grouped to form a plurality of capacitors. The attached aluminum anode sheet tabs are electrically connected to a feedthrough pin of an anode feedthrough extending through the case or compartment wall. In the above-referenced '851 patent, each of the anode sheet tabs are welded together and then welded to a post of a feedthrough pin. The single sheet cathode layers are also fabricated with cathode tabs that are also gathered together and electrically connected to a feedthrough pin of a cathode feedthrough extending through the case or compartment wall or connected to the electrically-conductive capacitor case wall.

Capacitor volume can be reduced slightly by interposing and welding a shared anode tab in between two adjacent anode sheets in the anode stack, as described, for example, in the above-referenced '388 patent. No particular method of welding is disclosed, and the interposed stack of anode tabs would thicken and distort the anode sheet stack making it difficult to fit into a flatsided capacitor housing.

In another approach described in U.S. Pat. No. 5,584,890, the center anode sheet of a three-sheet anode layer is fabricated with an inward recess into which an anode tab is inserted. The three anode sheets are joined together at a distance from the anode tab by using cold welding, although laser welding and arc welding are mentioned as alternatives without detail.

In the above-referenced '133 patent, a single anode tab is fitted into a slot of one of the stacked anode sheets and attached to one or more of the adjoining anode sheets by cold welding. The anode sheets are cold welded together at more than one location by use of a press and press fixture having spring-loaded or pneumatically driven cold weld pins that extend through pin bores of a top plate and a base plate bearing against the uppermost and lowermost exposed surfaces of the stack of anode sheets to be cold welded together.

By necessity, the joinder of anode sheets together to form multi-sheet anode layers and to separate anode tabs by such techniques must break through the oxide layer over the exposed etched surfaces of the anode sheets and fill or compress the underlying etched surface until the valve metals of the sheet cores are in intimate contact such that a low resistance electrical connection is achieved. Typically, it is necessary to provide multiple attachment sites to provide redundancy, which increases reliability. But breaking through the etched oxide layers of the multiple sheets in multiple places reduces the overall capacitance. Moreover, the attachment techniques can damage the etched oxide layers adjacent to the points of attachment or across the exposed outermost anodized surfaces of the outermost sheets of the anode layer.

Thus, there is a need for further reducing capacitor volume, increasing capacitor reliability, and reducing cost and complexity of the capacitor manufacturing process for high voltage electrolytic capacitors used in ICDs and other IMDs and other electric circuit applications.

SUMMARY OF THE INVENTION

The present invention provides for methods and apparatus for securely mechanically and electrically attaching anode sheets of multi-sheet anode layers of electrolytic capacitors together in a simple manner that minimizes the connection area and does not unduly damage formed surfaces of the anode sheets.

In accordance with the present invention, the side-by-side stacked multiple anode sheets of a multi-sheet anode layer are joined together by at least one malleable member that is fitted through a bore extending through each sheet and expanded in the aligned anode sheet bores to bear against the valve metal core layers of the anode sheets.

In a process in accordance with the invention, anode sheet bores are made through the anode sheets in the process of the sheet fabrication at locations that enable the axial alignment of the anode sheet bores into an anode layer bore when the anode sheets are stacked together to form an anode layer. The anode layer bore has an anode layer bore length corresponding to the sheet stack height of the side-by-side stacked anode sheets. A malleable member is inserted into each anode layer bore comprising the aligned anode sheet bores. Force is applied substantially only to the malleable member to compress it longitudinally and expand it laterally against the exposed valve metal of each anode sheet to effectively cold-weld the malleable member with the valve metal. In one sense, the expansion of the malleable conductive member functions as an expansion rivet, and these terms shall be used Interchangeably herein.

Preferably, the malleable conductive member comprises a pin fitted through the aligned anode sheet bores, and the axially applied forces longitudinally compress and laterally expand the pin to interference fit against the valve metal of the anode sheets. The pin and the anode sheet bores forming the anode layer bore have a compatible cross-section shape so that the pin can be inserted into the anode layer bore. The pin length preferably exceeds the anode layer bore length by a predetermined amount. The pin length and the bore size and the cross-section size of the pin are selected so that the pin expansion normal to the applied force is sufficient to apply welding force against the anode sheets to weld them to the malleable member thereby making a unitary anode layer without fracturing or distorting the anode sheets. In the process, the pin is shortened until the pin length equals the anode layer bore length and is flush with the outermost surfaces of the anode layer, that is, the outer exposed surfaces of the outer anode sheet of the anode.

The bore and pin are preferably circular. If the bore is non-cylindrical, the pin is preferably keyed in cross-section shape to fit the cross-section shape of the aligned anode sheet bores or otherwise dimensioned to fit the cross-section shape of the aligned anode sheet bores.

Or the malleable conductive member can comprise a plurality of malleable pellets fitted through the aligned first and second bores such that the stacked pellet height in the aligned anode sheet bores exceeds the stack height and anode layer bore length of the side-by-side stacked anode sheets by a predetermined amount. Then, the malleable pellets are compressed by force applied axially thereto so that the pellets are welded together and are substantially flush with the outermost surfaces of the anode layer. The stacked pellet height, the bore and pellet sizes, and the cross-section shapes are selected so that the pellet expansion normal to the applied force is sufficient to apply sufficient force against the anode sheets to weld the valve metal core layers of the anode sheets to the welded together stack of pellets, thereby making a unitary anode layer without fracturing or distorting the anode sheets.

The bore is preferably circular and the malleable pellets are preferably cylindrical or spherical. If the bore Is non-cylindrical, the malleable pellets are keyed to or otherwise fit the cross-section shape of the aligned anode sheet bores.

The malleable conductive member and the anode sheets are preferably fabricated from the same valve metal, e.g., aluminum. Preferably, the anode sheets of the anode layer are attached using a plurality of such bores and malleable conductive members.

The method of the invention is preferably also employed to fix an anode tab to the anode sheets of the anode layer. At least one anode sheet is fabricated having a slot or notch into which the anode tab is fitted. The remaining anode sheets are fabricated with sheet bores that are axially aligned to extend across or traverse the notch when the anode sheets are stacked together. The anode tab is fabricated with a tab bore that is aligned with the aligned anode sheet bores that traverse the notch when the anode tab is inserted into the notch. The malleable member is then inserted into the aligned sheet and tab bores and compressed to affix the anode sheets and tab together.

The resulting anode layer of the present invention then comprises a first anode sheet formed of a valve metal having first and second sheet sides that are bounded by a sheet edge, the first anode sheet having a first bore extending from the first sheet side to the second sheet side and at least one second anode sheet formed of a valve metal having first and second sheet sides that are bounded by a sheet edge, the first anode sheet having a second bore extending from the first sheet side to the second sheet side. A malleable conductive member or expansion rivet is interference fitted through the first and second bores and into physical and electrical contact with the valve metal of the first and second sheets, whereby the valve metal of the first and second sheets are electrically and mechanically connected together.

Preferably, the anode layer further comprises an anode tab fitted In a notch of the first anode sheet and attached to the second anode sheet by a malleable member traversing a third bore through the second anode sheet and a tab bore traversing the anode tab and axially aligned with the third bore.

Advantageously, any number of two or more anode sheets can be coupled together following the teachings of the present invention. A robust electrical and mechanical connection of the anode sheets of the anode layer is achieved through the present invention. In addition, compressive forces applied to the malleable conductive members only compress and expand the malleable conductive members in the aligned anode sheet bores. Compression and damage of the etched and anodized layers of the anode sheets is minimized as applied force is confined substantially to compression of the malleable conductive members, and a high capacitance per unit area is achieved.

A capacitor is assembled from the anode layer, a cathode layer, and a separator between the anode layer and the cathode layer and fitted into a capacitor case with appropriate electrical connections made from the anode and cathode tabs to respective anode and cathode terminals of the capacitor. Or, a capacitor layer is assembled from the anode layer, a cathode layer, and a separator between the anode layer and the cathode layer, a plurality of the capacitor layers are stacked into a capacitor sub-assembly and fitted into a capacitor case, and the anode and cathode tabs of the capacitor layers are electrically interconnected to anode and cathode terminals of the capacitor.

In one embodiment, an exemplary electrolytic capacitor formed in accordance with the present invention comprises an electrode stack assembly and electrolyte located within the interior case chamber of a hermetically sealed capacitor case. The electrode stack assembly comprises a plurality of capacitor layers stacked in registration upon one another, each capacitor layer comprising a cathode layer having a cathode tab, an anode layer comprising at least one anode sheet having an anode tab, and a separator layer located between adjacent anode and cathode layers, whereby all adjacent cathode layers and anode layers of the stack are electrically insulated from one another by a separator layer. Anode terminal means extend through the capacitor case sidewall for electrically connecting a plurality of the anode tabs to one another and providing an anode connection terminal at the exterior of the case. Cathode terminal means extend through or to an encapsulation area of the capacitor case side wall for electrically connecting a plurality of the cathode tabs to one another and providing a cathode connection terminal at the exterior of the case. A connector assembly is electrically attached to the anode connection terminal for making electrical connection with the anode tabs and to the cathode connection terminal for making electrical connection with the cathode tabs.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other aspects and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIGS. 3(a)-3(g) are exploded perspective views of the manner in which the various components of the exemplary ICD IPG of FIGS. 1 and 2, including the electrolytic capacitors of the present invention, are disposed within the housing of the ICD IPG;

FIG. 7 Is a side cross-section view taken along line 7—7 of FIG. 6 showing the anode sheets expansion riveted together in accordance with the preferred embodiments of the present invention;

FIGS. 8(a)-8(d) are alternative cross-sections of the circular cross-section bores and mating malleable conductive members depicted in FIGS. 6 and 7;

FIGS. 9(a) and 9(b) are side cross-section views taken along lines 7—7 of FIG. 6 showing the steps of expansion riveting the anode sheets together employing pins sized and keyed to fit the cross-section of the aligned anode sheet bores in accordance with a first embodiment of the invention to electrically and mechanically join the valve metals of the anode layers;

FIGS. 10(a) and 10(b) are side cross-section views taken along lines 7—7 of FIG. 6 showing the steps of expansion riveting the anode sheets together employing a plurality of pellets sized and keyed to fit the cross-section in accordance with a second embodiment of the invention to electrically and mechanically join the valve metals of the anode layers;

FIG. 14 is a plan view of the completed embodiment of an electrolytic capacitor in accordance with the invention.

DETAILED DESCRIPTION OF THE PREFERRED EMBODIMENTS

A preferred embodiment of the present invention is described herein in relation to an ICD IPG without limitation as to other uses of electrolytic capacitors fabricated in accordance with the general principles of the invention. The following described capacitor and ICD takes the overall form of those disclosed in the above-referenced, commonly assigned '133 and related patents, but the present invention can be employed in the fabrication of electrolytic capacitors of any configuration used in ICDs, other IMDs and in other applications. While the present invention can be practiced using valve metals of any type, aluminum is employed in the preferred embodiments described herein.

Figure 1:
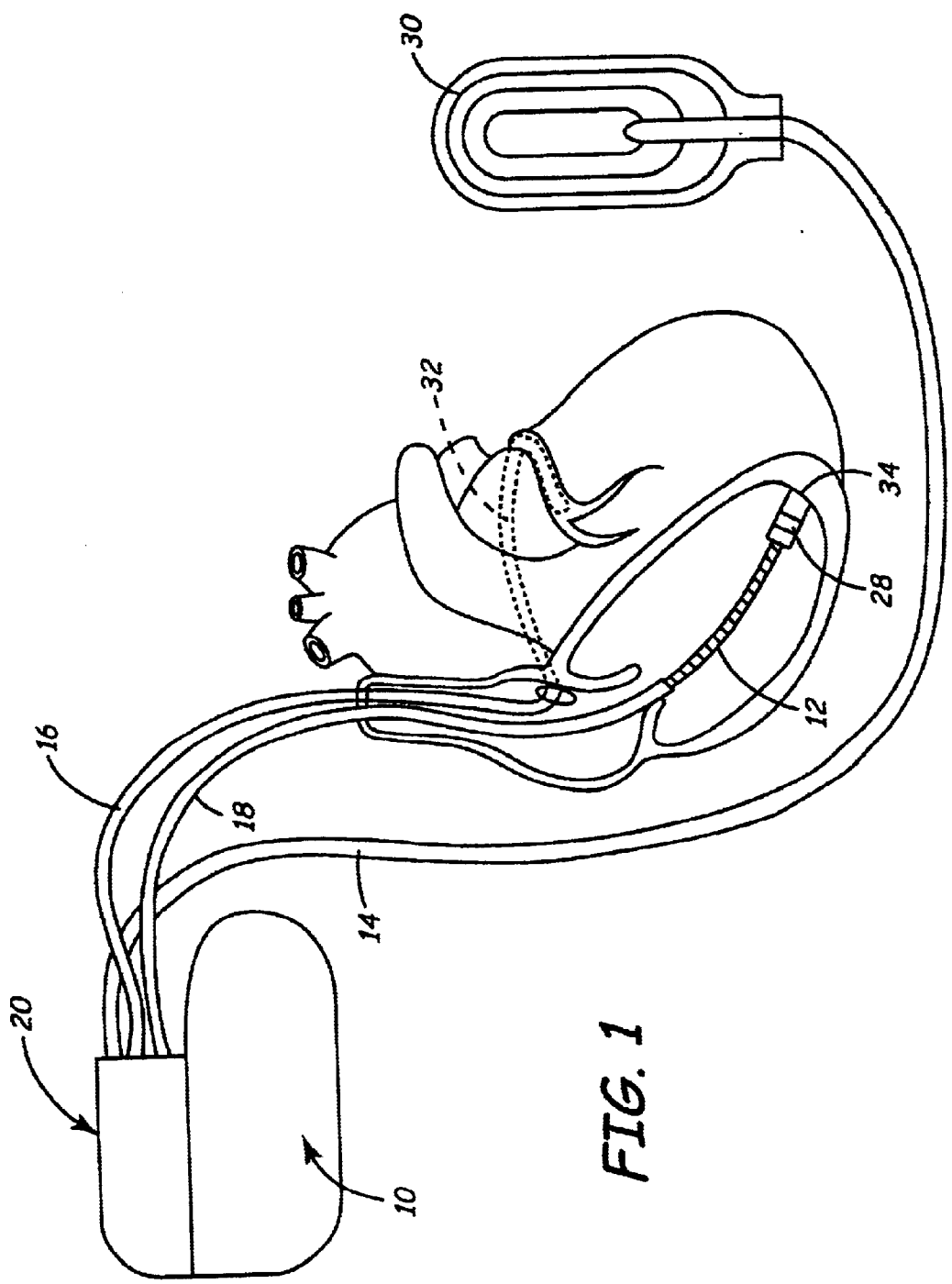
FIG. 1 illustrates the physical components of one exemplary embodiment of an ICD IPG and lead system in which the present Invention may be advantageously incorporated.

FIG. 1 illustrates one embodiment of ICD IPG 10 in which the capacitor of the present invention is advantageously Incorporated, the associated ICD electrical leads 14, 16 and 18, and their relationship to a human heart 12. The leads are coupled to ICD IPG 10 by means of multi-port connector block 20, which contains separate connector ports for each of the three leads illustrated. Lead 14 is coupled to subcutaneous electrode 30, which is intended to be mounted subcutaneously in the region of the left chest. Lead 16 is a coronary sinus lead employing an elongated coil electrode, which is located in the coronary sinus and great vein region of the heart. The location of the electrode is illustrated in broken line format at 32, and extends around the heart from a point within the opening of the coronary sinus to a point in the vicinity of the left atrial appendage.

Lead 18 is provided with elongated electrode coil 28, which is located in the right ventricle of the heart. Lead 18 also includes stimulation electrode 34 that takes the form of a helical coil that is screwed into the myocardial tissue of the right ventricle. Lead 18 may also include one or more additional electrodes for near and far field electrogram sensing.

In the system illustrated, cardiac pacing pulses are delivered between helical electrode 34 and elongated electrode 28. Electrodes 28 and 34 are also employed to sense electrical signals indicative of ventricular contractions. As illustrated, it is anticipated that the right ventricular electrode 28 will serve as the common electrode during sequential and simultaneous pulse multiple electrode defibrillation regimens. For example, during a simultaneous pulse defibrillation regimen, pulses would simultaneously be delivered between electrode 28 and electrode 30 and between electrode 28 and electrode 32. During sequential pulse defibrillation, it is envisioned that pulses would be delivered sequentially between subcutaneous electrode 30 and electrode 28 and between coronary sinus electrode 32 and right ventricular electrode 28. Single pulse, two electrode defibrillation shock regimens may be also provided, typically between electrode 28 and coronary sinus electrode 32. Alternatively, single pulses may be delivered between electrodes 28 and 30. The particular interconnection of the electrodes to an ICD will depend somewhat on which specific single electrode pair defibrillation shock regimen is believed more likely to be employed.

Figure 2:
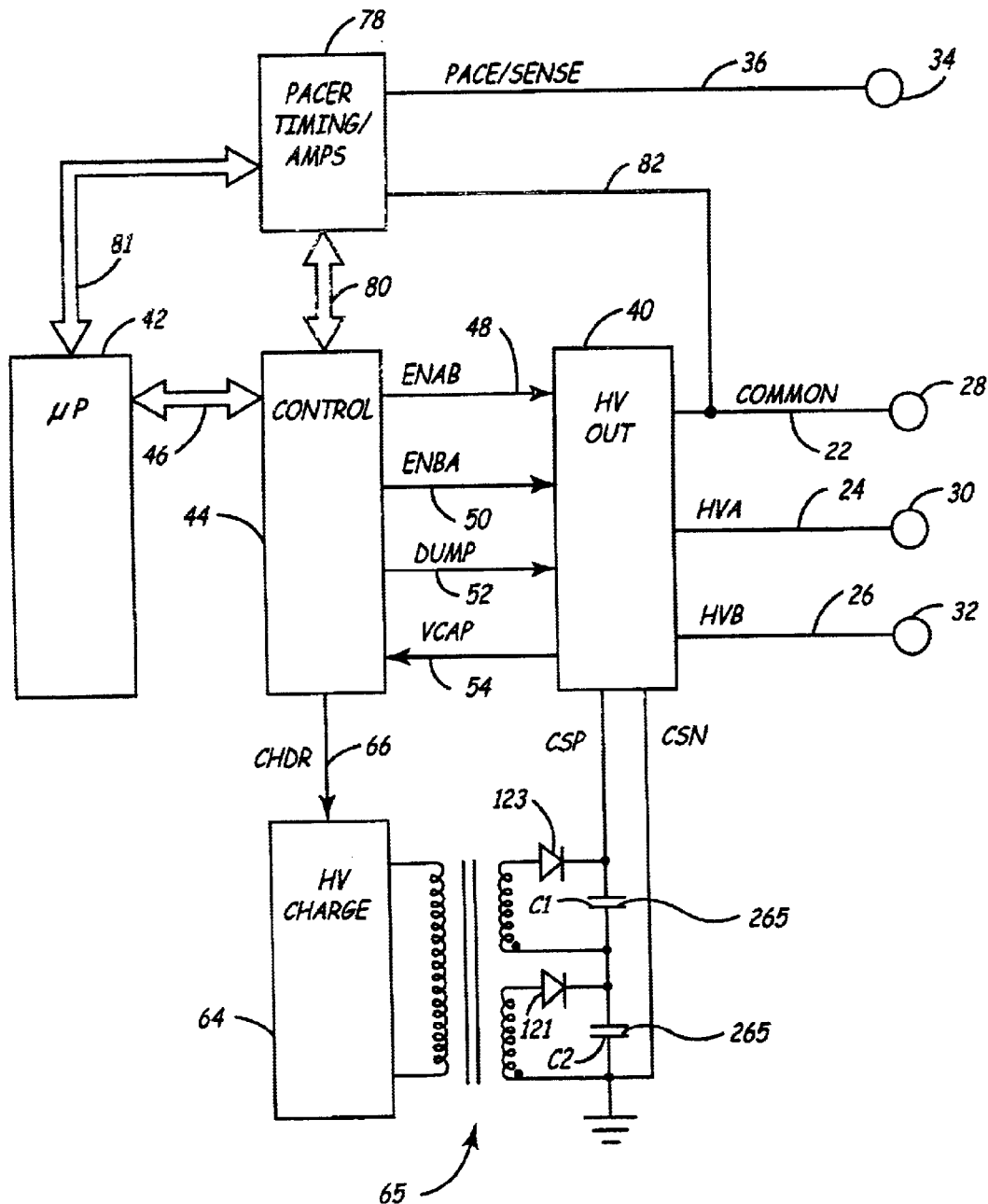
FIG. 2 is a simplified functional block diagram illustrating the interconnection of voltage conversion circuitry with the high voltage capacitors of the present Invention with the primary functional components of one type of an ICD.

FIG. 2 is a block diagram illustrating the interconnection of high voltage output circuit 40, high voltage charging circuit 64 and capacitors 265 according to one example of the microcomputer based operating system of the ICD IPG of FIG. 1. As illustrated, the ICD operations are controlled by means of a stored program in microprocessor 42, which performs all necessary computational functions within the ICD. Microprocessor 42 is linked to control circuitry 44 by means of bi-directional data/control bus 46, and thereby controls operation of the output circuitry 40 and the high voltage charging circuitry 64. Pace/sense circuitry 78 awakens microprocessor 42 to perform any necessary mathematical calculations, to perform tachycardia and fibrillation detection procedures and to update the time intervals controlled by the timers in pace/sense circuitry 78 on reprogramming of the ICD operating modes or parameter values or on the occurrence of signals indicative of delivery of cardiac pacing pulses or of the occurrence of cardiac contractions,.

The basic operation and particular structure or components of the exemplary ICD of FIGS. 1 and 2 may correspond to any of the systems known in the art, and the present invention is not dependent upon any particular configuration thereof. The flat aluminum electrolytic capacitor of the present invention may be employed generally in conjunction with the various systems illustrated in the aforementioned '209 patent, or in conjunction with the various systems or components disclosed in the various patents listed in the above-referenced '133 patent Control circuitry 44 provides three signals of primary importance to output circuitry 40. Those signals include the first and second control signals discussed above, labelled here as ENAB, line 48, and ENBA, line 50. Also of importance is DUMP line 52, which initiates discharge of the output capacitors, and VCAP line 54 that provides a signal indicative of the voltage stored on the output capacitors C1, C2, to control circuitry 44. Defibrillation electrodes 28, 30 and 32 illustrated in FIG. 1, above, are shown coupled to output circuitry 40 by means of conductors 22, 24 and 26. For ease of understanding, those conductors are also labelled as "COMMON", "HVA" and "HVB". However, other configurations are also possible. For example, subcutaneous electrode 30 may be coupled to HVB conductor 26, to allow for a single pulse regimen to be delivered between electrodes 28 and 30. During a logic signal on ENAB, line 48, a cardioversion/defibrillation shock is delivered between electrode 30 and electrode 28. During a logic signal on ENBA, line 50, a cardioversion/defibrillation shock Is delivered between electrode 32 and electrode 28.

The output circuitry includes a capacitor bank, including capacitors C1 and C2 and diodes 121 and 123, used for delivering defibrillation shocks to 5 the electrodes. Alternatively, the capacitor bank may include a further set of capacitors as depicted in the above referenced '758 application. In FIG. 2, capacitors 265 are illustrated in conjunction with high voltage charging circuitry 64, controlled by the control/timing circuitry 44 by means of CHDR line 66. As illustrated, capacitors 265 are charged by means of a high frequency, high voltage transformer 65. Proper charging polarities are maintained by means of the diodes 121 and 123. VCAP line 54 provides a signal indicative of the voltage on the capacitor bank, and allows for control of the high voltage charging circuitry and for termination of the charging function when the measured voltage equals the programmed charging level.

Pace/sense circuitry 78 includes an R-wave sense amplifier and a pulse generator for generating cardiac pacing pulses, which may also correspond to any known cardiac pacemaker output circuitry and includes timing circuitry for defining ventricular pacing intervals, refractory intervals and blanking intervals, under control of microprocessor 42 via control/data bus 80.

Control signals triggering generation of cardiac pacing pulses by pace/sense circuitry 78 and signals indicative of the occurrence of R-waves, from pace/sense circuitry 78 are communicated to control circuitry 44 by means of a bidirectional data bus 81. Pace/sense circuitry 78 is coupled to helical electrode 34 illustrated in FIG. 1 by means of a conductor 36. Pace/sense circuitry 78 is also coupled to ventricular electrode 28, illustrated in FIG. 1, by means of a conductor 82, allowing for bipolar sensing of R-waves between electrodes 34 and 28 and for delivery of bipolar pacing pulses between electrodes 34 and 28, as discussed above.

Figure 3F:
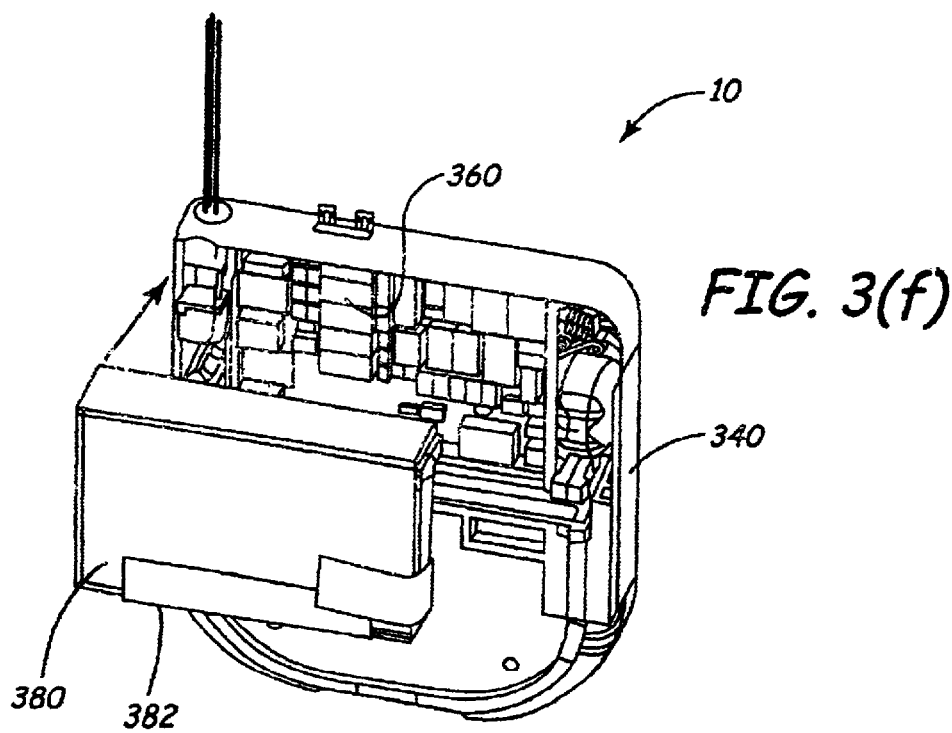
Figure 3G:
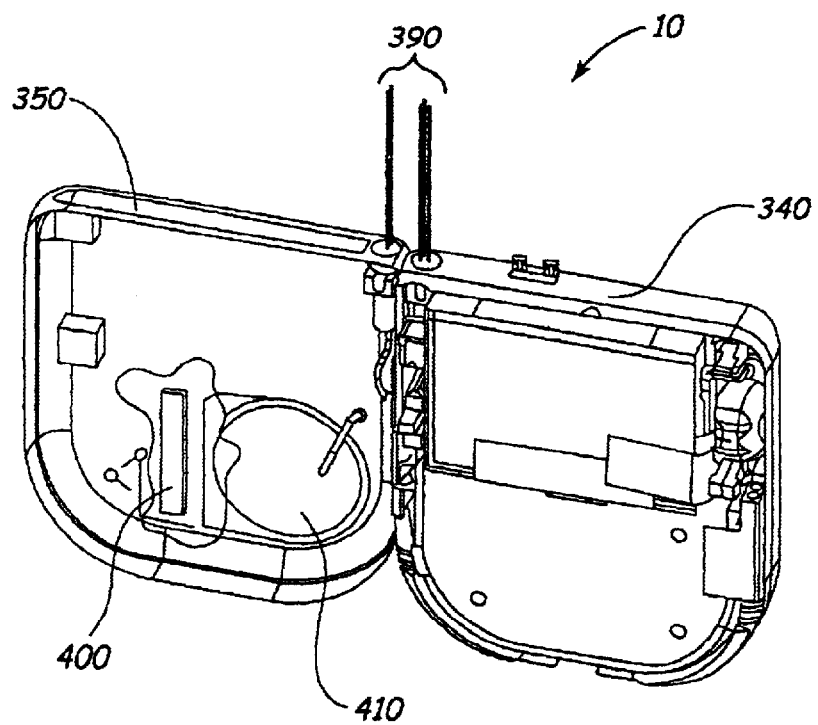

FIGS. 3(*a*) through 3(*g*) show perspective views of various components 30 of ICD IPG 10, including one embodiment of the capacitor of the present invention, as those components are placed successively within the housing of ICD IPG 10 formed by right and left hand shields 240 and 350.

In FIG. 3(*a*), electronics module 360 is placed in right-hand shield 340 of ICD IPG 10. FIG. 3(*b*) shows ICD IPG 10 once electronics module 360 has been seated in right-hand shield 340.

FIG. 3(*c*) shows a pair of capacitors 265 formed as described herein prior to being placed within right-hand shield 340, the capacitors 265 being connected electrically in series by interconnections in electronics module 340. FIG. 3(*d*) shows ICD IPG 10 once the pair of capacitors 265 has been placed within right-hand shield 340. It will be understood that other shapes of capacitors 265 can be inserted into the housing of ICD IPG 10 in the same or similar manner as described here.

FIG. 3(*e*) shows insulator cup 370 prior to its placing atop capacitors 265 in right-hand shield 340. FIG. 3(*f*) shows electrochemical cell or battery 380 having insulator 382 disposed around battery 380 prior to placing it in shield 340. Battery 380 provides the electrical energy required to charge and re-charge capacitors 265, and also powers electronics module 360. Battery 380 may take any of the forms employed in the prior art to provide cardioversion/defibrillation energy, some of which are identified in above referenced, commonly assigned, '133 patent.

FIG. 3(*h*) shows ICD IPG 10 having left-hand shield 350 connected to right-hand shield 340 and feedthrough 390 projecting upwardly from both shield halves. Activity sensor 400 and patient alert apparatus 410 are shown disposed on the side lower portion of left-hand shield 350. Left-hand shield 350 and right-hand shield 340 are subsequently closed and hermetically sealed (not shown in the figures).

Figure 4:
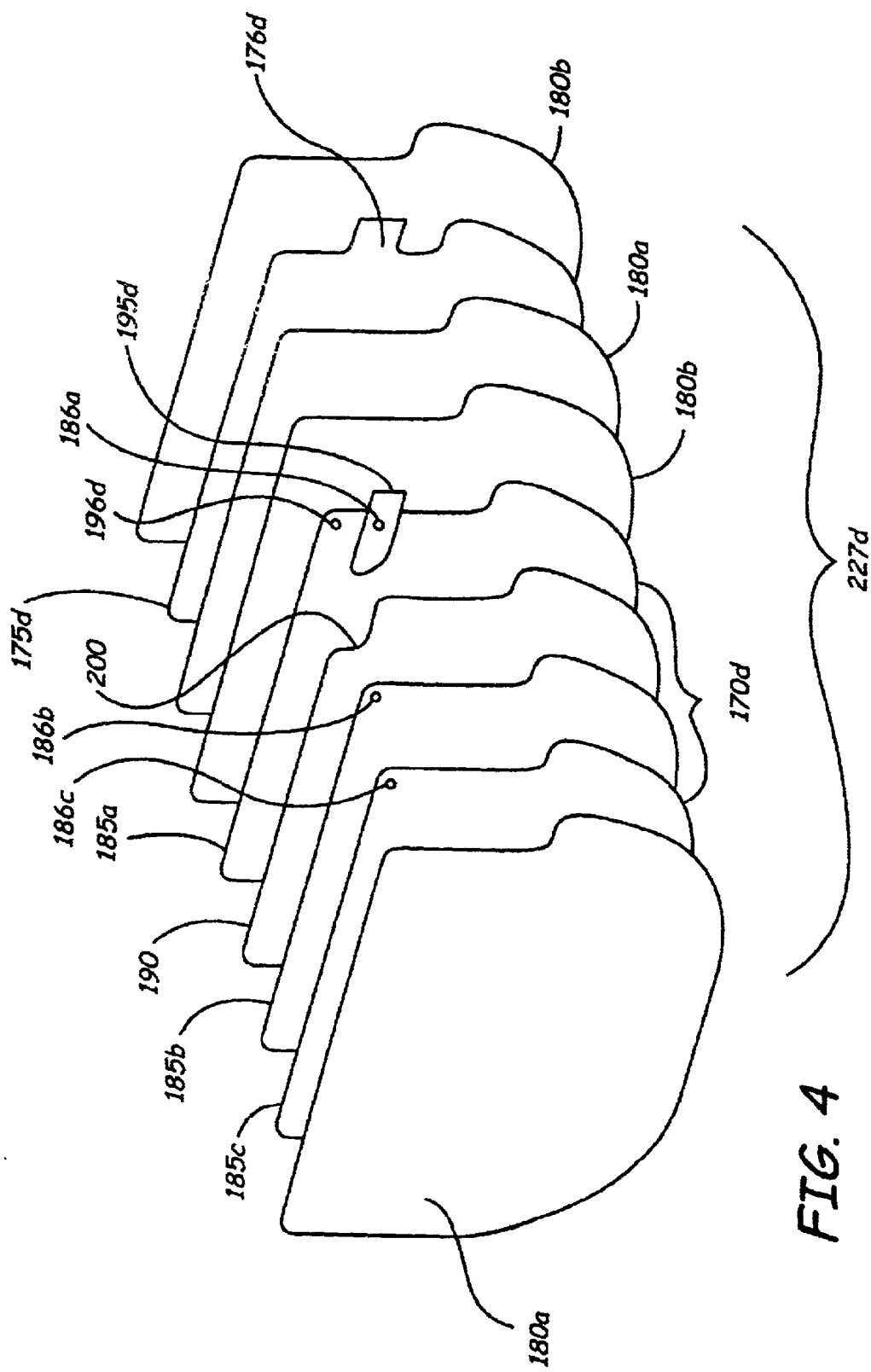
FIG. 4 is an exploded view of one embodiment of a single capacitor layer of an electrolytic capacitor incorporating the present invention.

FIG. 4 shows an exploded view of one embodiment of an anodecathode sub-assembly or capacitor layer 227 of capacitor 265 in which the present invention may be implemented. It will be understood that the teachings of the present invention can be employed in the fabrication of and in the resulting capacitors employing a single cathode layer, a single anode layer formed of a plurality of anode sheets assembled together and to an anode tab as described herein, and a separator separating the anode layer and cathode layer.

The exemplary capacitor design described herein employs a stacked configuration of a plurality of capacitor layers 227 as further described below with respect to FIG. 5. Each capacitor layer 227 comprises alternating substantially rectangular-shaped anode layers 170 and cathode layers 175, with a substantially rectangular-shaped separator layer 180 being interposed therebetween. The shapes of anode layers 170, cathode layers 175 and separator layers 180 are primarily a matter of design choice, and are dictated largely by the shape or configuration of case 90 within which those layers are ultimately disposed. Anode layers 170, cathode layers 175 and separator layers 180 may assume any arbitrary shape to optimize packaging efficiency.

The exemplary anode layer 170d most preferably comprises a plurality of non-notched anode sheets 185 designated 185a, 185b. 185c, and notched anode sheet 190, including anode tab notch 200, that are expansion riveted together in accordance with the present invention, and anode tab 195 that is expansion riveted to anode sheets 185a, 185b and 185c in accordance with the present Invention. It will be understood that anode layer 170d shown in FIG. 4 is but one possible embodiment of an anode layer 170. Exemplary cathode layer 175d most preferably is fabricated of a single sheet of aluminum foil and has cathode tab 176 formed integral thereto and projecting from the periphery thereof.

Individual anode sheets 185a, 185b, 190 and 185c (alternatively referred to as anode sheets 185/190 herein) are cut from high-purity aluminum foil formed as described above to achieve high capacitance per unit area. Thin anode sheets 185/190 are preferred, especially if they substantially maintain or increase specific capacitance while reducing the thickness of the electrode stack assembly 225, or maintain the thickness of electrode stack assembly 225 while increasing overall capacitance. For example, it is contemplated that individual anode sheets 185/190 have a thickness of between about 10 micrometers and about 500 micrometers.

Cathode layer 175 is preferably a single cathode sheet cut from high purity, flexible, aluminum foil. Cathode layer 175 is most preferably cut from aluminum foil having high surface area (i.e., highly etched cathode foil), high specific capacitance (preferably at least 200 microfarads/cm$^2$, and at least 250 microfarads/cm$^2$ when fresh), a thickness of about 30 micrometers, a cleanliness of about 1.0 mg/m$^2$ respecting projected area maximum chloride contamination, and a purity which may be less than corresponding to the starting foil material from which anode foil Is made. The cathode foil preferably has an initial purity of at least 99% aluminum, and more preferably yet of about 99.4% aluminum, a final thickness of about 30 micrometers, and an initial specific capacitance of about 250 microfarads per square centimeter. In other embodiments, cathode foil has a specific capacitance ranging between about 100 and about 500 microfarads/cm$^2$, and a thickness ranging between about 10 and about 150 micrometers.

It is generally preferred that the specific capacitance of the cathode foil be as high as possible, and that cathode layer 175 be as thin as possible. For example, it is contemplated that individual cathode layers 175 have a specific capacitance of about 100–1,000 microfarads/cm$^2$. Suitable cathode foils are commercially available on a widespread basis. In still other embodiments, the cathode foil comprises materials or metals in addition to aluminum, aluminum alloys and "pure" aluminum.

Separator layer sheets 180a and 180b and outer separator layers of the electrode stack assembly 225 (FIG. 8) fabricated from a plurality of stacked capacitor layers 227 are most preferably made from a roll or sheet of separator material. Separator layers 180 are preferably cut slightly larger than anode layers 170 and cathode layers 175 to accommodate misalignment during the stacking of layers, to prevent subsequent shorting between anode and cathode layers, and to otherwise ensure that a physical barrier is disposed between the anodes and the cathodes of the finished capacitor.

In one preferred embodiment of the capacitor layer 227 as depicted in FIG. 4, two individual separator layer sheets 180a and 180b form the separator layer 180 that is disposed between each anode layer 170 and cathode layer 175. Further single separator layer sheets 180a and 180b are disposed against the outer surfaces of the anode sheet 185c and the cathode layer 175d. When the sub-assemblies are stacked, the outermost single separator layer sheets 180a and 180b bear against adjacent outermost single separator layer sheets 180b and 180a, respectively, of adjacent capacitor layers so that two sheet separator layers 180 separate all adjacent cathode and anode layers of an electrode stack assembly 225.

It Is preferred that separator layer sheets 180a and 180b and exterior separator layers between the electrode stack assembly and the case and cover be fabricated of a material that (a) is chemically inert; (b) is chemically compatible with the selected electrolyte; (c) may be impregnated with the electrolyte to produce a low resistance path between adjoining anode and cathode layers, and (d) physically separates adjoining anode and cathode layers. In one preferred embodiment, separator material is a pure cellulose, very low halide or chloride content Kraft paper having a thickness of about 0.0005 inches, a density of about 1.06 grams/cm$^3$, a dielectric strength of 1,400 Volts AC per 0.001 inches thickness, and a low number of conducting paths (about 0.4/ft$^2$ or less). Separator layer sheets 180a and 180b and outer separator layers 165a and 165b may also be fabricated of materials other than Kraft paper, such as Manila paper, porous polymeric materials or fabric gauze materials. In such capacitor stacks fabricated of a plurality of capacitor layers, a liquid electrolyte saturates or wets separator layers 180 and is disposed within the capacitor interior case chamber.

It will be understood by those skilled in the art that the precise number of capacitor layers 227 selected for use In a electrode stack assembly 225 will depend upon the energy density, volume, voltage, current, energy output and other requirements placed upon capacitor 265. Similarly, it will be understood by those skilled in the art that the precise number of notched anode sheets 190 and un-notched anode sheets 185, anode tabs 195, anode layers 170, cathode layers 175 and separator layers 180 selected for use in a given embodiment of capacitor layer 227 will depend upon the energy density, volume, voltage, current, energy output and other requirements placed upon capacitor 265. It will now become apparent that a virtually unlimited number of combinations and permutations respecting the number of capacitor layers 227, and the number of notched anode sheets 190 and un-notched anode sheets 185 forming anode layer 170, anode layers 170, anode tabs 195, cathode layers 175 and separator layers 180 disposed within each capacitor layer 227, may be selected according to the particular requirements of capacitor 265. In particular, while the described preferred embodiment of the invention relates to use of four anode sheets 185a, 185b, 185c, and 190, it will be appreciated that a larger or smaller number of anode sheets can be joined together to form an anode layer employing the teachings of the present invention.

Figure 5:
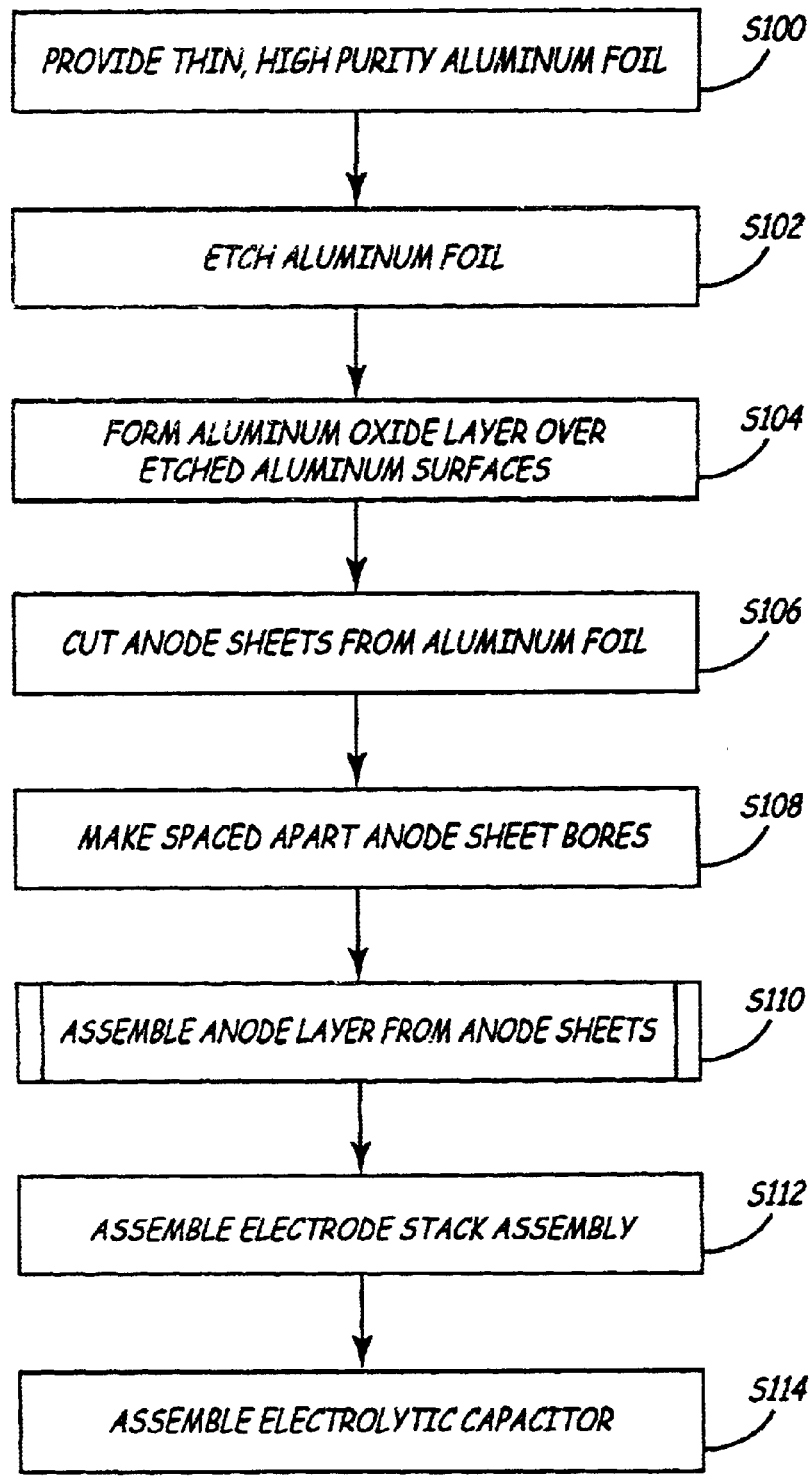
FIG. 5 is a flow chart illustrating the steps of forming an electrolytic capacitor in accordance with the invention.

FIG. 5 depicts the method of forming anode sheets, attaching the anode sheets together to form an anode layer and then fabricating an electrolytic capacitor using the anode layers. First, a thin aluminum foil of the type described above is provided in step S100, etched in step S102, "formed" in step S104, and cut into anode sheets 185/190 shown in FIG. 4 in step S106. The anodized, aluminum oxide, dielectric layers are grown in step over the pores and the tunnels created in the etching step S102 in a manner known in the art.

The anode sheets 185/190 have opposed major anode sheet surfaces that can be highly etched in step S102 to form certain pores extending part way through the thickness of anode sheet to a sheet core layer and certain through-etched tunnels extending all the way through the sheet core layer to provide electrolyte wetting through the outer anode sheets to inner anode sheets of an anode layer. The large pores, small pores, large cross-section tunnels, and small cross-section tunnels provide enhanced surface area in comparison to the planar sheet surfaces prior to etching. However, some surface area potential is lost by virtue of overly large pores and tunnels. Conversely, ESR is increased by small tunnels that impede electrolyte and ion passage therethrough. Preferably, the etched anode foil has a high specific capacitance (at least about 0.3, at least about 0.5 or most preferably at least about 0.8 microfarads/cm$^2$), has a dielectric withstand parameter of at least 425 Volts DC, a thickness ranging between about 50 and about 200 micrometers, and a cleanliness of about 1.0 mg/m$^2$ respecting projected area maximum chloride contamination. The anode foil preferably has a rated surge voltage of 390 Volts, an initial purity of about 99.99% aluminum, a final thickness of about 104 micrometers, plus or minus about five micrometers, and a specific capacitance of about 0.8 microfarads per square centimeter. Suitable anode foils etched to specification are commercially available on a widespread basis.

The anode and cathode sheets are most preferably cut to shape in step S106 using dies having low wall-to-wall clearance, where inter-wall spacing between the substantially vertically-oriented corresponding walls of the punch and die is most preferably on the order of about 6 millionths of an inch per side. Larger or smaller inter-wall spacings between the substantially vertically oriented corresponding walls of the punch and cavity, such as about 2–12 millionths of an inch may also be employed but are less preferred. The anode tab 195d is preferably cut from aluminum foil, and separator layers 180a, 180b are preferably cut from Kraft paper, respectively, in the same manner.

Such low clearance results in smooth, burr free edges along the peripheries of anode sheets 185 and 190 and anode tabs 195 as well as cathode layers 175, cathode tabs 176 and the separator layers 180a, 180b of each capacitor layer 170. Smooth, burr free edges on the walls of the dies have been discovered to be critical respecting reliable performance of a capacitor. The presence of burrs along the peripheries of anode sheets 185 and 190, anode and cathode tabs 195,176, cathode layers 175 and separator layers 180 may result in short circuit and failure of the capacitor. The means by which anode foil, cathode foil, and separator materials are cut may have a significant impact on the lack or presence of burrs and other cutting debris disposed about the peripheries of the cut members. The use of low clearance dies produces an edge superior to the edge produced by other cutting methods, such as steel rule dies. The shape, flexibility and speed of a low clearance die have been discovered to be superior to those achieved by laser or blade cutting. Other methods of cutting or forming anode sheets 185 and 190, anode tabs 195, cathode layers 175 and separator layers 180 include, but are not limited to, steel rule die cutting, laser cutting, water jet cutting and blade cutting. Further details relating to preferred methods of cutting the anode foil to form anode sheets and sandwiching anode sheets together to form an anode layer 170 are set forth in the above-referenced, commonly assigned, '133 patent.

In this way, a first anode sheet 190 is fabricated of an etched and formed valve metal sheet having first and second sheet sides that are bounded by a common sheet edge, the first anode sheet having an anode receiving notch 200 Into which anode tab 195d can be inserted and physically and electrically coupled to at least one second anode sheets, in this example, anode sheet 185a, 185b, 185c. The second anode sheets 185a, 185b, 185c are fabricated of etched and formed valve metal sheets having first and second sheet sides that are bounded by a common sheet edge. Next, it is necessary to make a first anode sheet bore extending through the first and anode sheet and second anode sheet bores through each of the second anode sheets 185a, 185b, 185c, from the first sheet side to the second sheet side in each case such that the first and second sheet that can be substantially axially aligned when the first and second anode sheet bores are aligned when the anode sheets 185/190 are stacked to be assembled into the anode layer 170d. Preferably, a plurality of such axially aligned first and second anode sheet bores are formed. Moreover, preferably a tab bore 196 is formed through the anode tab 195d that is fitted into notch 200 of the first anode sheet 190 so that the tab bore 196 is aligned with anode sheet bores 186a, 186b, 186c to form an aligned anode bore 205c depicted in FIGS. 6, 7, 9(a)-9(b), and 10(a)-10(b).

Therefore, in accordance with the present invention, a plurality of aligned anode layer bores, e.g., the illustrated four anode layer bores 205a, 205b, 205c, 205d shown in FIGS. 6, 7, 9(a)–9(b), and 10(a)–10(b), are made through the anode sheets 185/190 in step S108. The anode layer bores are preferably made by any puncturing process e.g., by punching, mechanically 30 drilling, laser boring, water jet boring, etc. The sheet (and tab) bores that comprise anode layer bores 205a, 205b, 205c, 205d can be circular in cross-section or any convenient shape, e.g., the keyed bore shapes 205', 205", 205'", 205"" shown in FIGS. 8(a)-8(d).

Figure 6:
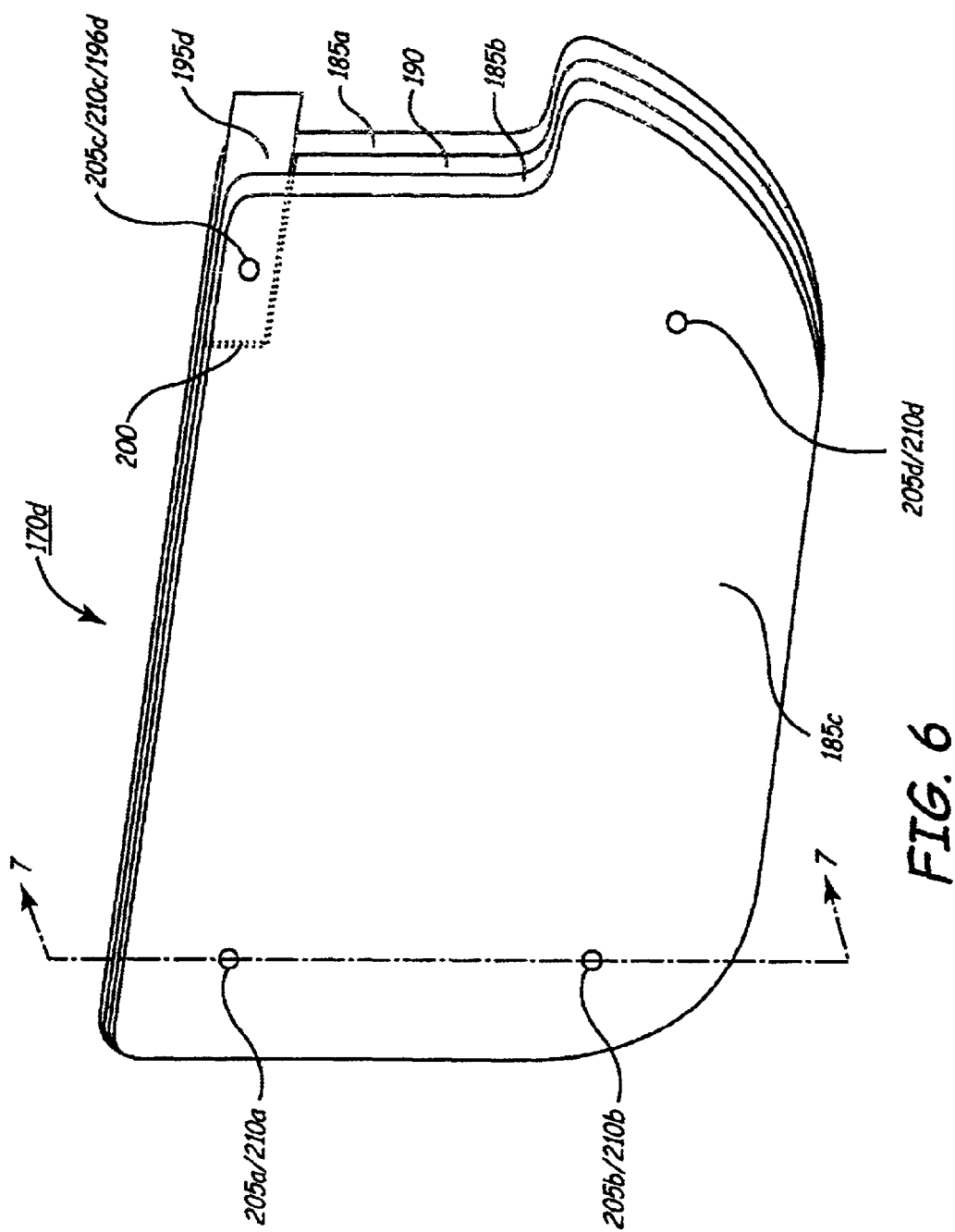
FIG. 6 is a perspective view of the anode layer assembled from anode sheets employing expansion riveting in accordance with the preferred embodiments of the invention.

In FIG. 5, the sheet bores, e.g., sheet bores 186a, 186b, 186c shown in FIG. 4, having a circular or non-circular shape are made in step S108 through the anode sheets 185/190 after or at the same time as the cutting step S106 and prior to the anode layer assembly step S110. The tab bore 196 can be made at the same time that the tab 195 is cut from valve metal foil. The sheet bores are located through each of the anode sheets 185/190 so as to be substantially aligned axially to provide the substantially aligned anode layer bores when the anode sheets 185/190 are stacked. For example, automated boring equipment can be employed to precisely form the sheet bores through the sheets 185/190 as they are cut in step S106. Or, the sheets 185/190 can be stacked together in side-by-side relation as shown in FIGS. 6 and 7 and maintained in precise alignment as the anode layer bores 205a, 205b, 205c, 205d are made through the stacked sheets 185/190. For convenience of illustration, only the anode sheet bores 186c, 186c and 186d and the tab bore 196 are separately enumerated in the figures.

Thus, in accordance with the present invention, the anode sheets 185/190 are fabricated with a plurality of anode sheet bores extending through each anode sheet 185/190 that are aligned to form the plurality of aligned anode layer bores 205a, 205b, 205c, 205d. Each anode layer bores 205a, 205b, 205c, 205d has an anode layer bore length when the anode sheets 185/190 are side-by-side stacked in the anode layer 170d of FIG. 6 equal to the anode layer stack height.

In step S110, the anode sheets 185/190 of multi-sheet anode layer 170d are joined together by malleable members that are fitted into the anode layer bores 205a–205d and expanded therein to bear against the aluminum valve metal core layer between the anodized layers of the anode sheets 185/190 exposed by the bores and the anode tab 195. A malleable member is inserted into each anode layer bore 205a–205d, and force is applied substantially only to the malleable member to compress it to be substantially equal to the anode layer bore length and expand it normally to the applied force and against the exposed valve metal of the core layer of each anode sheet 185/190 or the anode tab 195 to effectively interference fit and expansion rivet the malleable member and the aluminum valve metal of each anode sheet and anode tab together.

FIG. 7 is a side cross-section view taken along line 7—7 of FIG. 6 showing the anode sheets 185a, 185b, 190 and 185c of FIGS. 4 and 6 expansion riveted together by a compressed rivets or malleable members 210a and 210b driven into respective anode layer bores 205a and 205b. Each anode sheet 185a, 185b, 190 and 190 is depicted in cross-section In FIG. 7 and in FIGS. 9(*a*), 9(*b*), 10(*a*) and 10(*b*) as having a valve metal core layer (that may be tunnel etched through in certain places as described above) that is sandwiched between opposed first and second major anode sheet surfaces as indicated by the broken lines, that are etched and formed as described above. The depicted anode layers have an anode stack thickness or height between the exposed major surfaces of the anode sheets 185a and 185c, and the compressed rivets or malleable members 210a and 210b have been compressed to the same stack height.

As noted above, the anode layer bores 205a–205d can be cylindrical due to a circular cross-section and the malleable members can be cylindrical. Alternatively, the anode layer bores 205a–205d can be non-cylindrical due to non-circular bore cross-sections, and exemplary star, polygon, cross-shaped, and oval bore cross-section shapes 205', 205", 205''', 205'''' are depicted in FIGS. 8(*a*)-8(*d*). In non-circular configuration, the malleable members would preferably be keyed in cross-section to fit the non-cylindrical bore cross-sections. While the anode layer bores and malleable members are depicted as preferably extending perpendicularly to the plane and through the stacked anode sheets 185/190, it will be understood that they can be directed at other angles to the planes of the stacked anode sheets 185/190.

Preferably, in one embodiment depicted in FIGS. 9(*a*) and 9(*b*), the malleable conductive members comprise the pins 215a–215d fitted through the anode layer bores 205a–205d, respectively, as shown in FIG. 9(*a*) and axially compressed by application of forces F1, F2 as shown in FIG. 9(*b*) to interference fit against the valve metal of the anode sheets 185/190. The pins 215a–215d and the anode layer bores 205a–205d have a compatible shape and dimensions so that the pins 215a–215d can be inserted through the anode layer bores 205a–205d, respectively. The pin length preferably exceeds the anode layer bore length of the side-by-side stacked anode sheets 185/190 as shown in FIG. 9(*a*). The stack height, the pin length, the bore size, and the cross-section size of each pin 215a–215d are selected so that the pin expansion normal to the applied forces F1, F2 is sufficient to apply welding force against the anode sheets 185/190 to weld them to the pins 215a–215d thereby forming a unitary anode layer 170d without fracturing or distorting the anode sheets 185/190. The anode layer bores 205a–205d and pins 215a–215d are preferably circular.

If the anode layer bores 205a–205d non-cylindrical, e.g., as is shown In FIGS. 8(*a*)-8(*d*), then the pins 215a–215d are preferably keyed to fit the cross-section of the anode layer bores 205a–205d. However, a pin having a different cross-section than the bore can be employed as long as the pin can be inserted into the bore prior to application of the compressive forces F1, F2 to expand outward into the bore and surrounding anode sheets.

The applied forces F1, F2 depicted in FIG. 9(*b*) axially compress the pin length until it Is equal to the stack height, whereby the pins 215a–215d are flush with the outermost surfaces of the stacked sheets forming the anode layer 170d. Preferably forces F1, F2 are applied only to the pins 215a–215d or additionally to a minimally sized area of the anode layer 170d substantially surrounding each of the bores 205a–205d.

Or the malleable conductive member can comprise a stack of malleable pellets 220a–220d fitted through or stacked up in the anode layer bores 205a–205d, respectively, as shown in FIG. 10(*a*) and axially compressed by forces F1, F2 as shown in FIG. 10(*b*) to interference fit against the valve metal of the anode sheets 185/190. Each of the malleable pellets 220a–220d and the anode layer bores 205a–205d have a compatible shape so that the malleable pellets 220a–220d can be stacked in the anode layer bores 205a–205d, respectively. The pellet stack height preferably exceeds the stack height of the side-by-side stacked anode sheets 185/190 as shown in FIG. 10(*a*). The stacks of malleable pellets 220a–220d are compressed by forces F1, F2 applied axially thereto as shown In FIG. 10(*b*) so that the pellets 220a–220d are welded together and are substantially flush with the outermost surfaces of the anode layer 170d assembled from the stacked anode sheets 185/190. The stack height, the initial stacked pellet height, and the relative pellet and bore cross-section sizes are selected so that the pellet expansion normal to the applied forces F1, F2 is sufficient to apply sufficient force against the anode sheets 185/190 to weld them to the joined together malleable pellets 220a–220d thereby forming a unitary anode layer 170d without fracturing or distorting the anode sheets 185/190. The applied forces F1, F2 depicted in FIG. 10(*b*) axially compress the stacks of pellets until the pellet height is equal to the anode layer stack height, whereby the welded together stack of pellets 220a–220d are flush with the outermost surfaces of the stacked sheets forming the anode layer 170d. Preferably forces F1, F2 are applied only to the stacks of pellets 220a–220d or additionally to a minimally sized area of the anode layer 170d substantially surrounding each of the bores 205a–205d.

The anode layer bores 205a–205d is preferably circular, and each of the malleable pellets 220a–220d are preferably cylindrical or spherical. If the anode layer bores 205a–205d are non-cylindrical as depicted in FIGS. 8(*a*)-8(*c*), for example, the malleable pellets 220a–220d are preferably keyed to fit the cross-section shape of the anode layer bores 205a–205d. The keying can be identical with relatively close tolerances to enable insertion of the pellets into the bores for lateral expansion of the pellets in the bores as the pellet stack is compressed by forces F1, F2. Or pellets 220a–220d having a different cross-section than the bores 205a 205d can be employed as long as the pellets can be inserted into the bore prior to application of the compressive forces F1, F2.

The stack of anode sheets 185/190 can be positioned in a press and maintained in alignment by the malleable pins 215a–215d or stack of malleable pellets 220a–220d inserted into the respective anode layer bores 205a–205d and/or by a frame or alignment pin array abutting the aligned edges of the stack of anode sheets 185/190. The assembly is placed in a press having upper and lower planar press plates that are brought together to apply the forces F1, F2 against the pin or stack ends. The press plates are brought together until they contact the outermost surfaces of the anode layer 170d, that is the exposed surfaces of anode sheets 185a and 185c in this particular embodiment. The minimum separation of the distance between the press plates can be preset to equal the anode sheet stack height or limited by a force sensor or a physical stop that prevents the further compression of the malleable member(s)).

The malleable conductive members, e.g., the cylindrical rods or pins 210a–210d of FIGS. 9(a)-9(b) or pellet stacks 215a–215d of FIGS. 10(a)-10(b) are preferably also fabricated of the same ductile valve metal as the core layers of the anode sheet 185a, 185b, 185c, and 190, e.g. aluminum. The particular shape, number and manner of fabrication and formation of the anode sheets of the anode layer 170d described herein is merely illustrative, and does not limit the scope of the present invention in any way. Among other things, the present invention can be employed to electrically and mechanically connect the valve metal cores of any number of stacked, etched and anodised, anode sheets and any configurations of the anode sheets.

Figure 11:
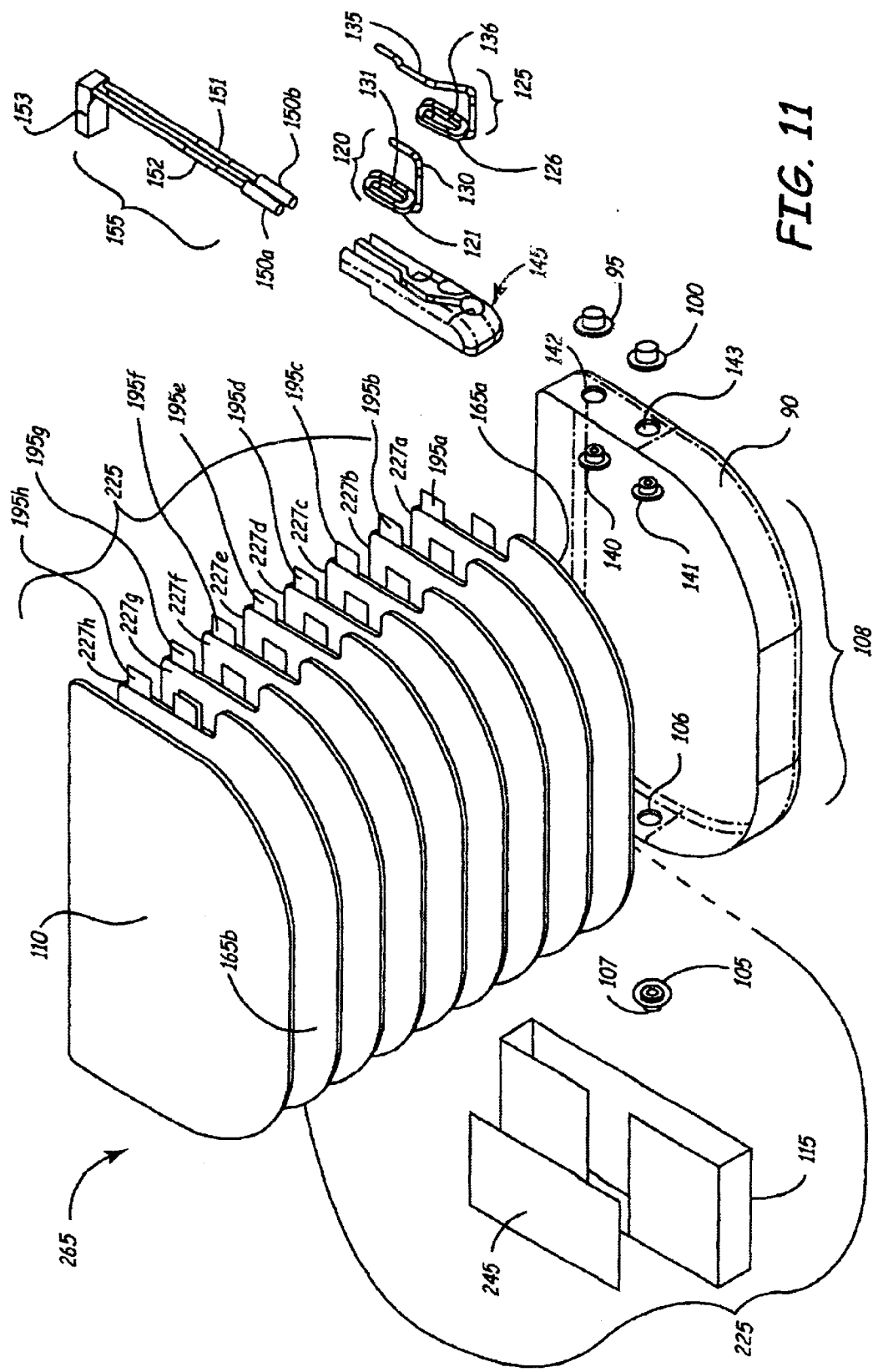
FIG. 11 is an exploded top perspective view of one embodiment of a series of capacitor layers each incorporating the anode layers of the present invention ready to be assembled into a electrode stack assembly and fitted together with the remaining components of one embodiment of an electrolytic capacitor.
Figure 12:
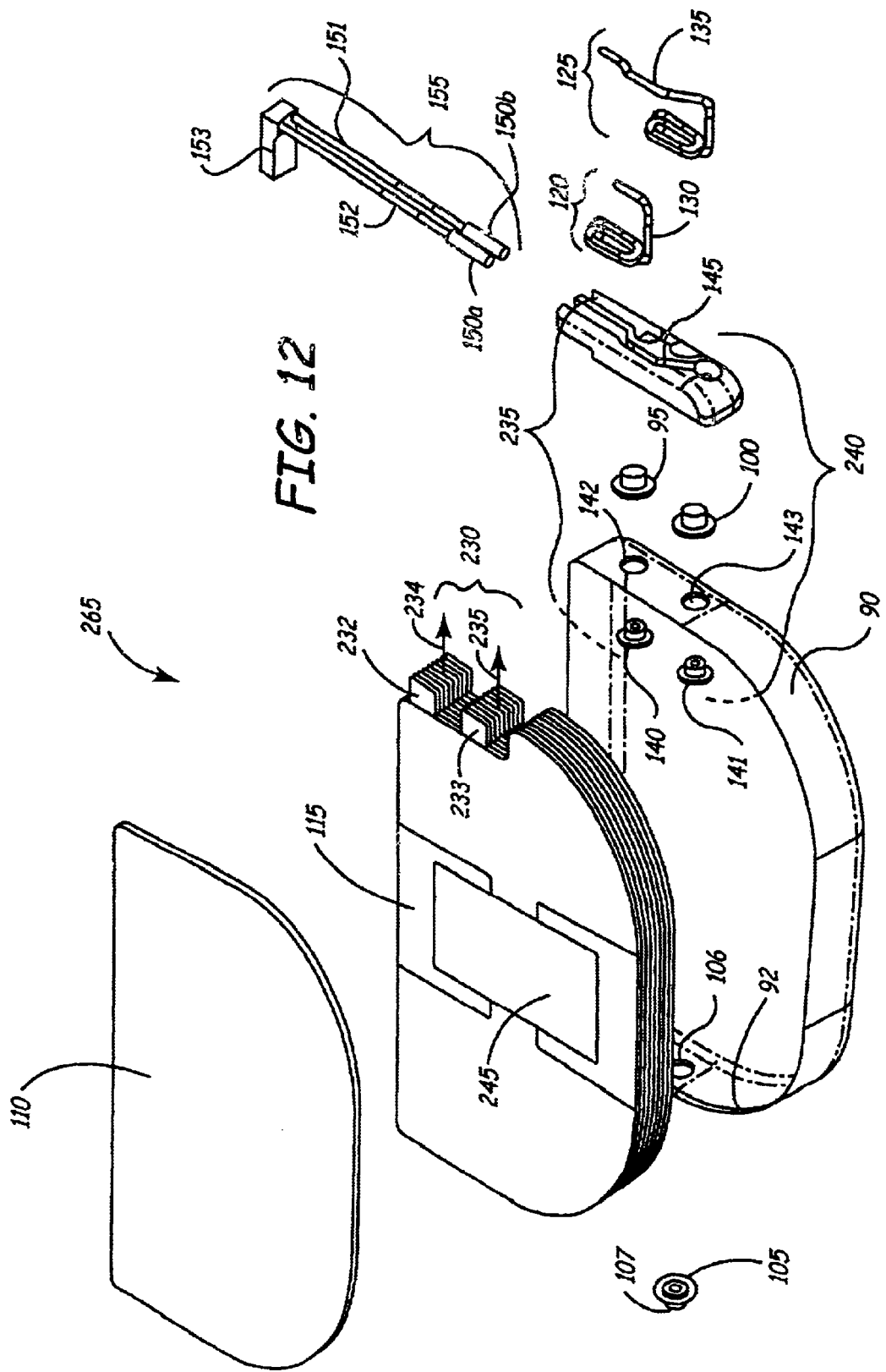
FIG. 12 is an exploded top perspective view of the electrode stack assembly ready to be fitted together with the remaining components of the embodiment of an electrolytic capacitor.

FIGS. 11 and 12 illustrate the formation of the electrode stack assembly 225 in accordance with step S112 of FIG. 5 in relation to the capacitor case cover 110, the case housing 90 and other components of the capacitor 265 illustrated in FIG. 8. The electrode stack assembly 225 comprises a plurality of capacitor layers 227a–227h fabricated as described above with reference to FIG. 4 and having anode tabs 195a–195h and cathode tabs 176a–176h. The voltage developed across each capacitor layer disposed within electrode stack assembly 225 most preferably ranges between about 360 and about 390 Volts DC. As described below, the various anode subassemblies of electrode stack assembly 225 are typically connected in parallel electrically, as are the various cathode layers of electrode stack assembly 225. The electrode stack assembly 225 is merely illustrative, and does not limit the scope of the present invention in any way respecting the number or combination of anode layers 170, cathode layers 175, separator layers 180, anode tabs 195, cathode tabs 176, and so on. The number of electrode components is instead determined according to the total capacitance required, the total area of each layer, the specific capacitance of the foil employed and other factors.

The capacitor layers 227a 227h are stacked together between outer paper layers 165a and 165b, and outer wrap 115 is folded over the top of electrode stack assembly 225 in step S112. Wrapping tape 245 is then holds outer wrap 115 in place and secures the various components of electrode stack assembly 225 together. Outer wrap 115 is most preferably die cut from separator material described above or other suitable materials such as polymeric materials, suitable heat shrink materials, suitable rubberized materials and synthetic equivalents or derivatives thereof, and the like. Wrapping tape 245 is most preferably cut from a polypropylene-backed acrylic adhesive tape, but may also be replaced by a staple, an ultrasonic paper joint or weld, suitable adhesives other than acrylic adhesive, suitable tape other than polypropylene-backed tape, a hook and corresponding clasp and so on. Usable alternatives to outer wrap 115 and wrapping tape 245 and various stacking and registration processes by which electrode stack assembly 225 is most preferably made are not material to the present invention and are disclosed in the above-referenced, commonly assigned, '133 patent.

FIG. 12 shows an exploded top perspective view of one embodiment of an exemplary, case neutral, electrolytic capacitor 265 employing the electrode stack assembly 225 therein and the electrical connections made to the gathered anode and cathode tabs 232 and 233. This embodiment includes anode feedthrough 120 and cathode feedthrough 125 most preferably having coiled basal portions 121 and 126, respectively. Feedthroughs 120 and 125 provide electrical feedthrough terminals for capacitor 265 and gather gathered anode tabs 232 and gathered cathode tabs 233 within basal portions 121 and 126 for electrical and mechanical interconnection.

Feedthrough wire is first provided and trimmed to length for construction of feedthroughs 120 and 125. One end of the trimmed wire is coiled such that its Inside diameter or dimension is slightly larger than the diameter or dimension required to encircle gathered anode tabs 232 or gathered cathode tabs 233. Gathered anode tabs 232 are next gathered, or brought together in a bundle by crimping, and inside diameter 131 of anode feedthrough coil assembly 120 is placed over gathered anode tabs 232 such that anode feedthrough pin 130 extends outwardly away from the base of gathered anode tabs 232. Similarly, gathered cathode tabs 233 are gathered and inside diameter 136 of cathode feedthrough coil assembly 125 is placed over gathered cathode tabs 233 such that cathode feedthrough pin 135 extends outwardly away from the base of cathode tab 233. Coiled basal portions 121 and 126 of anode and cathode feedthroughs 120 and 125 are then most preferably crimped onto anode and cathode tabs 232 and 233, followed by trimming the distal ends thereof, most preferably such that the crimps so formed are oriented substantially perpendicular to imaginary axes 234 and 235 of gathered anode and cathode tabs 232 and 233. Trimming the distal ends may also, but less preferably, be accomplished at other non-perpendicular angles respecting imaginary axes 234 and 235.

In some preferred methods, a crimping force is applied to feedthrough coils 121 and 126 and tabs 232 and 233 throughout a subsequent preferred welding step. In one method, it is preferred that the crimped anode and cathode feedthroughs be laser or ultrasonically welded along the top portion of the trimmed edge of the distal ends to anode and cathode tabs 232 and 233. Following welding of feedthroughs 120 and 125 to gathered anode tabs 232 and gathered cathode tabs 233, respectively, pins 130 and 135 are bent for insertion through feedthrough holes 142 and 143 of case 90.

Many different embodiments of the feedthroughs and means for connecting the feedthrough pins to anode and cathode tabs exist other than those shown explicitly in the figures and are described in the above-referenced, commonly assigned, '133 patent.

A case sub-assembly is also created from case 90, anode ferrule 95, cathode ferrule 100, and fill port ferrule 105 are first provided. In a preferred embodiment of capacitor 265, the case 90 and cover 110 are fabricated of aluminum. In other embodiments, case 90 or cover 110 may be fabricated of any other suitable corrosion-resistant metal such as titanium or stainless steel, or may alternatively be fabricated of a suitable plastic, polymeric material or ceramic. The anode ferrule 95 and cathode ferrule 100 are welded to the aluminum case sidewall to fit around anode and cathode feedthrough ferrule holes 142 and 143, and a fill port ferrule is welded to the case sidewall around a fill port hole 106. The welding steps form no part of the present invention and various ways of doing so are disclosed in detail in the above-referenced, commonly assigned, '133 patent.

Wire guides 140 and 141 fit within center holes of ferrules 95 and 100 respectively and receive, center, and electrically insulate anode and cathode pins 130 and 135 from the case 90, anode ferrule 95, and cathode ferrule 100. The formation and assembly of the wire guides 140,141 with the ferrules 95,100 and cathode pins 130, 135 form no part of the present invention and examples thereof are disclosed in detail in the above-referenced, commonly assigned, '133 patent. Similarly, the insertion of the cathode pins 130, 135 through the wire guides 140,141 and the seating of the electrode stack assembly 225 coupled thereto into the interior case chamber of case 90 form no part of the present invention and examples thereof are disclosed in detail in the above-referenced, commonly assigned, '133 patent.

A connector assembly is also coupled with the exposed, outwardly extending pins 130 and 135. In one preferred embodiment, connector block 145 is disposed atop or otherwise connected to case 90 and/or cover 110, and has wire harness 155 attached thereto and potting adhesive disposed therein. However, the particular configuration of connector block 145 and its method of fabrication do not play a role in the practice of the present invention. Examples thereof are disclosed in detail in the above-referenced, commonly assigned, '133 patent.

Figure 13:
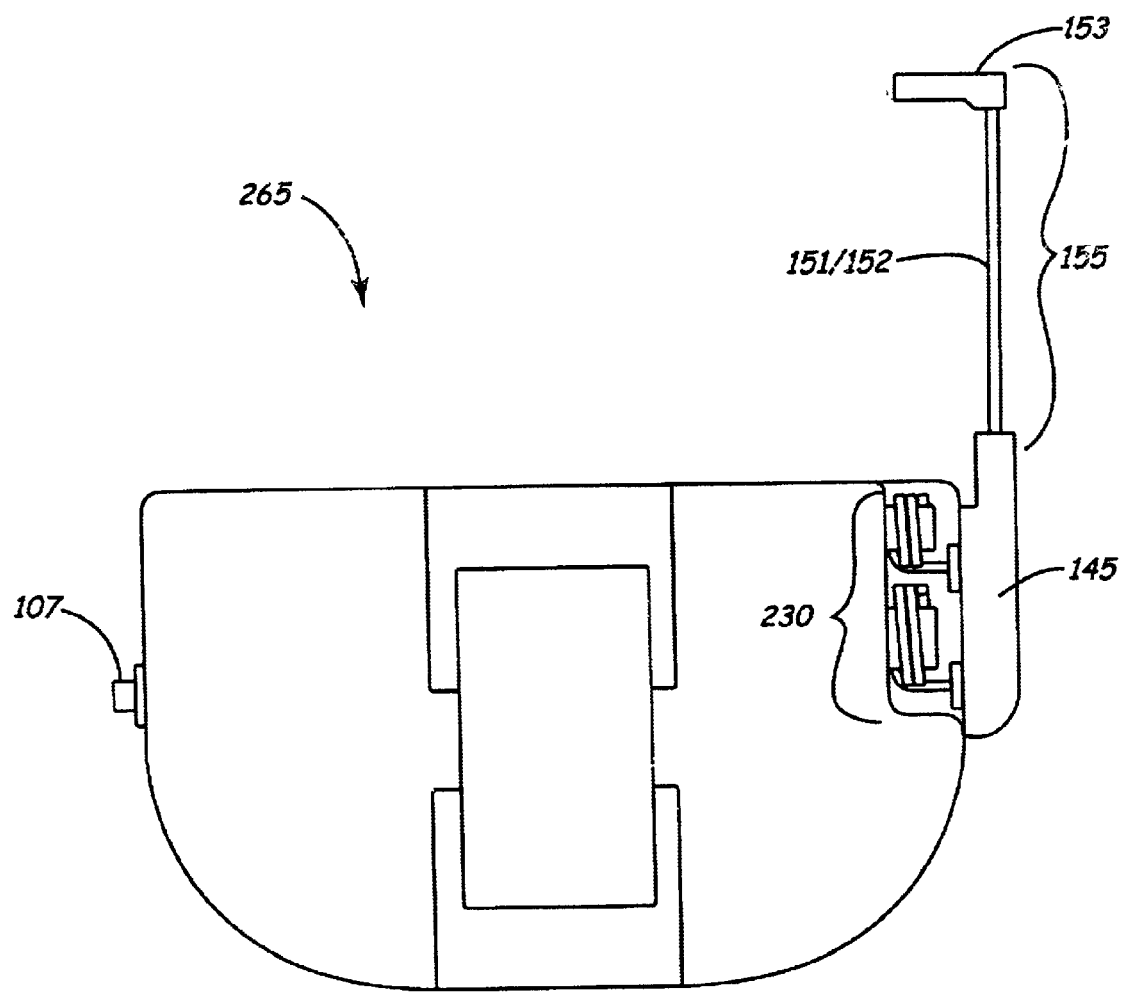
FIG. 13 is a plan view of the electrode stack assembly fitted into the capacitor housing together and attached to the remaining components of the embodiment of an electrolytic capacitor prior to attaching the cover to the housing and filling the capacitor with electrolyte.

In the illustrated embodiment, pre-formed plastic connector block 145 is placed on anode ferrule 95 and cathode ferrule 100 by guiding anode feedthrough pin 130 through connector block anode feedthrough hole 300, and then guiding cathode feedthrough pin 135 through connector block cathode feedthrough hole 305. Connector block 145 is next seated flush against the exterior surface of case 90. Anode feedthrough pin 130 is then inserted into anode crimp tube 150b of wire harness 155. Cathode feedthrough pin 135 is then inserted Into cathode crimp tube 150a of wire harness 155. Crimp tubes 150a and 150b are then crimped to feedthrough pins 130 and 135. The distal or basal portions of crimp tubes 150a and 150b are crimped on insulated anode lead 151 and insulated cathode lead 152, respectively. An epoxy adhesive is then injected into voids In the connector block 145 to insulate the crimped connections, seal the wire guides 140 and 141, case 90 and ferrules 95 and 100, and provide strain relief to feedthrough pins 130 and 135 and to the feedthrough wire crimp connections. Insulated leads 151 and 152 are likewise connected to terminal connector 153 that forms the female end of a slide contact and is adapted to be connected to electronics module 360 in FIG. 3(d). The completed assembly Is depicted in FIG. 13.

The life of capacitor 265 may be appreciably shortened if solvent vapor or electrolyte fluid escapes from the interior of capacitor 265. Moreover, if capacitor 265 leaks electrolyte, the electrolyte may attack the circuits to which capacitor 265 is connected, or may even provide a conductive pathway between portions of that circuit. The cover 110 is placed upon the upper edge 92 of the case side wall, the upper edge 92 is crimped over the cover edge, and the joint therebetween is laser welded all in a manner disclosed in the above-referenced 133 patent, for example, that forms no part of the present invention. The resulting capacitor 265 depicted in FIG. 14 thus most preferably includes hermetic laser welded seams between joint case 90 and cover 110, and between ferrules 95, 100, and 105 and case 90. Additionally, anode feedthrough portion 236 and cathode feedthrough portion 240 most preferably have an adhesive seal disposed therein for sealing the ferrule walls and the feedthrough wires.

The interior of capacitor 265 not occupied by the electrode stack assembly 225 is filled with electrolyte through the fill port 107 welded at fill port ferrule 105 into hole 106, aging cycles are conducted, and the fill port is then closed. The filling and aging are accomplished in a plurality of vacuum impregnation cycles and aging cycles form no part of the present invention and examples thereof are disclosed in detail in the above-referenced, commonly assigned, '133 patent. The electrolyte may be any suitable liquid electrolyte for high voltage electrolytic capacitors. In a preferred embodiment of the present invention, the electrolyte is an ethylene glycol based electrolyte having an adipic add solute. It is contemplated that other liquid electrolytes suitable for use in high voltage capacitors may also be employed.

During capacitor charging, the ethylene glycol based electrolyte releases hydrogen gas that accumulates within the interior capacitor chamber and eventually can cause the base and cover to bulge outward. In accordance with a preferred embodiment of the present invention, hydrogen gas is released through the lumen of fill port 107 while loss of liquid or vaporized electrolyte is prevented.

It will be understood that the capacitor 265 may alternatively be fabricated as a case negative capacitor where case 90 and cover 110 are electrically connected to the cathode layers and are therefore at the same electrical potential as the cathode layers, i.e., at negative potential.

The preceding specific embodiments are illustrative of a capacitor structure and method of fabrication thereof in accordance with the present invention. It is to be understood, therefore, that other expedients known to those skilled in the art or disclosed herein, and existing prior to the filing date of this application or coming into existence at a later time may be employed without departing from the invention or the scope of the appended claims.

All patents and printed publications disclosed herein are hereby incorporated by reference herein Into the specification hereof, each in its respective entirety.

We claim:

1. An electrode stack assembly of an electrolytic capacitor comprising:
   an anode layer comprising:
   a first anode sheet fabricated of a valve metal having first and second sheet sides that are bounded by a first sheet edge, the first anode sheet having a first anode sheet bore extending through the valve metal from the first sheet side to the second sheet side;
   at least one second anode sheet fabricated of a valve metal having first and second sheet sides that are bounded by a second sheet edge, the second anode sheet having a second anode sheet bore extending through the valve metal from the first sheet side to the second sheet side; and
   a first malleable conductive member expansion riveted within the first and second anode sheet bores into physical and electrical contact with the valve metals of the first and second anode sheets, whereby the valve metal of the second sheet is electrically connected to the valve metal of the first anode sheet;

a cathode layer; and a separator between the anode layer and the cathode layer, the separator carrying an electrolyte.

2. The electrode stack assembly of claim 1, further comprising a further second anode sheet each having a second anode sheet bore, one second anode sheet located against the first sheet side of the first anode sheet and the other second anode sheet located against the second sheet side of the first anode sheet, whereby the first and second anode sheet bores are axially aligned, and the first malleable conductive member is expansion riveted within the aligned first anode sheet bore and second anode sheet bores to the first and second anode sheets.

3. The electrode stack assembly of claim 2, wherein the first anode sheet further comprises a notch extending into the first anode sheet edge, and further comprising:

an anode tab comprising a first tab portion shaped to fit into the notch and a second tab portion outwardly extending from the first anode sheet edge and an anode tab bore extending through the first tab portion;

further second anode sheet bore formed through the second anode sheets in alignment with the anode tab bore; and a second malleable conductive member expansion riveted within the aligned further second anode sheet bores and the anode tab bore, whereby the anode tab is physically and electrically coupled to the valve metal of the second anode sheets.

4. The electrode stack assembly of claim 1, wherein the first malleable conductive member is fabricated of a pin fitted through the aligned first and second anode sheet bores and axially compressed to be expansion riveted to the valve metal of the first and second anode sheets.

5. The electrode stack assembly of claim 4, wherein the aligned first and second anode sheet bores have an anode layer bore length, and the pin fitted into the aligned first and second anode sheet bores has a pin length that exceeds the anode layer bore length that is shortened to substantially the anode layer bore length when the pin length is compressed and the pin is expanded in the aligned first and second anode sheet bore.

6. The electrode stack assembly of claim 1, wherein the first malleable conductive member is fabricated of a plurality of malleable pellets fitted through the aligned first and second anode sheet bores and axially compressed to be expansion riveted together and to the valve metal of the first and second anode sheets.

7. The electrode stack assembly of claim 6, wherein the aligned first and second anode sheet bores have an anode layer bore length, and the plurality of malleable pellets are stacked into the aligned first and second anode sheet bores having a pellet stack length that exceeds the anode layer bore length that is shortened to substantially the anode layer bore length when the pellet stack length is compressed and the malleable pellets are expanded In the aligned first and second anode sheet bore.

8. The electrode stack assembly of claim 1, wherein the aligned first and second anode sheet bores are substantially circular.

9. The electrode stack assembly of claim 1, wherein the aligned first and second anode sheet bores are non-circular.

10. The electrode stack assembly of claim 1, wherein the first anode sheet further comprises a notch extending Into the first anode sheet edge, and further comprising:

an anode tab comprising a first tab portion shaped to fit into the notch and a second tab portion outwardly extending from the first anode sheet edge and an anode tab bore extending through the first tab portion;

a further second anode sheet bore formed through the second anode sheet in alignment with the anode tab bore; and a second malleable conductive member expansion riveted within the aligned further second anode sheet bore and the anode tab bore, whereby the anode tab is physically and electrically coupled to the valve metal of the second anode sheet.

11. An electrode stack assembly of an electrolytic capacitor comprising:

an anode layer comprising:

a first anode sheet fabricated of a valve metal having first and second sheet sides that are anodized and bounded by a sheet edge, the first anode sheet having a plurality of first anode sheet bores extending through the valve metal from the first sheet side to the second sheet side;

at least one second anode sheet fabricated of a valve metal having first and second sheet sides that are anodized and bounded by a sheet edge, the second anode sheet having a plurality of second anode sheet bores extending through the valve metal from the first sheet side to the second sheet side; and a plurality of malleable conductive members expansion riveted within a respective plurality of anode layer bores each comprising a first anode sheet bore substantially aligned with a second anode sheet bore, the malleable conductive members making physical and electrical contact between the valve metals of the first and second anode sheets;

a cathode layer; and a separator between the anode layer and the cathode layer, the separator carrying an electrolyte.

12. The electrode stack assembly of claim 11, wherein said anode layer further comprises a pair of second anode sheets each having a plurality of second anode sheet bores, one second anode sheet located against the first sheet side of the first anode sheet and the other second anode sheet located against the second sheet side of the first anode sheet, whereby each of the plurality of second anode sheet bores is substantially aligned with a first anode sheet bore to form an anode layer bore, and the plurality of malleable conductive members are expansion riveted through the anode layer bores to make physical and electrical contact between the valve metals of the first and second anode sheets.

13. The electrode stack assembly of claim 12, wherein the first anode sheet further comprises a notch extending Into the first anode sheet edge, and further comprising:

an anode tab comprising a first tab portion shaped to fit into the notch and a second tab portion outwardly extending from the first anode sheet edge and an anode tab bore extending through the first tab portion;

one of said plurality of second anode sheet bores is made through the second anode sheet in alignment with the anode tab bore to form an anode layer bore; and one of said malleable conductive members is expansion riveted within the anode layer bore comprising the substantially aligned second anode sheet bores and the anode tab bore, whereby the anode tab is physically and electrically coupled to the valve metal of the second anode sheet.

14. The electrode stack assembly of claim 11, wherein the first anode sheet further comprises a notch extending into the first anode sheet edge, and further comprising:

an anode tab comprising a first tab portion shaped to fit into the notch and a second tab portion outwardly extending from the first anode sheet edge and an anode tab bore extending through the first tab portion;

one of said plurality of second anode sheet bores is made through the second anode sheet in alignment with the anode tab bore to form an anode layer bore; and one of said malleable conductive members is expansion riveted within the anode layer bore comprising the substantially aligned second anode sheet bore and the anode tab bore, whereby the anode tab is physically and electrically coupled to the valve metal of the second anode sheet.

15. The electrode stack assembly of claim 11, wherein the malleable conductive members are fabricated of pins fitted through the anode layer bores and axially compressed to be expansion riveted to the valve metal of the first and second anode sheets.

16. The electrode stack assembly of claim 11, wherein the malleable conductive members are fabricated of a plurality of malleable pellets fitted through the anode layer bores and axially compressed to be expansion riveted together and to the valve metal of the first and second anode sheets.

17. An electrode stack assembly of a capacitor comprising:
   a plurality of anode layers, each anode layer comprising:
      a first anode sheet fabricated of a valve metal having first and second sheet sides that are bounded by a sheet edge, the first anode sheet having a first anode sheet bore extending from the first sheet side to the second sheet side;
      at least one second anode sheet fabricated of a valve metal having first and second sheet sides that are bounded by a sheet edge, the second anode sheet having a second anode sheet bore extending from the first sheet side to the second sheet side; and
      a malleable conductive member expansion riveted through the first and second anode sheet bores and into physical and electrical contact with the valve metals of the first and second anode sheets, whereby the valve metal of the first and second anode sheets are electrically and mechanically connected together;
   a plurality of cathode layers; and
   a plurality of separators positioned between the anode layers and the cathode layers, the separators carrying an electrolyte.

18. The electrode stack assembly of claim 17, wherein at least one of said plurality of anode layers further comprise a pair of second anode sheets each having a second anode sheet bore, one second anode sheet located against the first sheet side of the first anode sheet and the other second anode sheet located against the second sheet side of the first anode sheet, whereby the first and second anode sheet bores are axially aligned, and the first malleable conductive member is expansion riveted within the aligned first anode sheet bore and second anode sheet bores to the first and second anode sheets.

19. The electrode stack assembly of claim 17, wherein:
   the first anode sheets have a plurality of first anode sheet bores extending through the valve metal from the first sheet side to the second sheet side;
   the second anode sheets have a plurality of second anode sheet bores extending through the valve metal from the first sheet side to the second sheet side; and
further comprising:
   a plurality of malleable conductive members expansion riveted within the plurality of substantially anode layer bores each comprising a first anode sheet bore and a second anode sheet bore into physical and electrical contact with the valve metals of the first and second anode sheets.

20. The electrode stack assembly of claim 19, wherein the first anode sheet further comprises a notch extending into the first anode sheet edge, and further comprising:
   an anode tab comprising a first tab portion shaped to fit into the notch and a second tab portion outwardly extending from the first anode sheet edge and an anode tab bore extending through the first tab portion;
   one of said plurality of second anode sheet bores is made through the second anode sheet in alignment with the anode tab bore to form an anode layer bore; and
   one of said malleable conductive members is expansion riveted within the anode layer bore comprising the substantially aligned second anode sheet bore and the anode tab bore, whereby the anode tab is physically and electrically coupled to the valve metal of the second anode sheet.

21. A method of fabricating an electrode stack assembly of an electrolytic capacitor comprising the steps of:
   assembling an anode layer by:
      providing first and second anode sheets fabricated of a valve metal having first and second sheet sides bounded by a sheet edge
      boring a first anode sheet bore through the first anode sheet from the first sheet side to the second sheet side;
      boring a second anode sheet bore through the second anode sheet from the first sheet side to the second sheet side;
      substantially aligning the first and second anode sheet bore; and
      expansion riveting a malleable conductive member within the first and second anode sheet bores into physical and electrical contact with the valve metals of the first and second anode sheets;
   providing a cathode layer, and
   interposing a separator between the anode layer and the cathode layer, the separator carrying an electrolyte.

22. The method of claim 21, wherein the step of assembling an anode layer further comprises:
   providing a further second anode sheet;
   boring a further second anode sheet bore through the further second anode sheet from the first sheet side to the second sheet side;
   fitting the second anode sheet against the first sheet side of the first anode sheet and the further second anode sheet against the second sheet side of the first anode sheet, whereby all of the first and second anode sheet bores are substantially axially aligned; and
   expansion riveting the malleable conductive member within the aligned first anode sheet bore and second anode sheet bores to the first and second anode sheets.

23. The method of claim 22, further comprising the steps of:
   providing the first anode sheet with a notch extending into the first anode sheet edge;
   providing an anode tab having a first tab portion shaped to fit into the notch and a second tab portion outwardly extending from the first anode sheet edge and an anode tab bore extending through the first tab portion;

boring second anode sheet bores through the second anode sheets at locations adapted to be aligned with the anode tab bore;

positioning the first tab portion of the anode tab within the notch to substantially align the second anode sheet bores and the anode tab bore; and expansion riveting a second malleable conductive member within the aligned second anode sheet bores and the anode tab bore, whereby the anode tab is physically and electrically coupled to the valve metal of the second anode sheets.

24. The method of claim 21, wherein the step of assembling an anode layer further comprises:

providing the first anode sheet with a notch extending into the first anode sheet edge;

providing an anode tab having a first tab portion shaped to fit into the notch and a second tab portion outwardly extending from the first anode sheet edge and an anode tab bore extending through the first tab portion;

boring a second anode sheet bore through the second anode sheet in alignment with the anode tab bore;

substantially aligning the second anode sheet bore and the anode tab bore; and expansion riveting a second malleable conductive member within the aligned second anode sheet bore and the anode tab bore, whereby the anode tab is physically and electrically coupled to the valve metal of the second anode sheet.

25. The method of claim 21, wherein the malleable conductive member is fabricated of a pin, and the expansion riveting step further comprises:

fitting the pin through the aligned first and second anode sheet bores; and axially compressing and normally expanding the pin against the valve metal of the first and second anode sheets.

26. The method of claim 21, wherein the aligned first and second anode sheet bores have an anode layer bore length, the malleable conductive member is fabricated of a pin having a pin length that exceeds the anode layer bore length, and the expansion riveting step further comprises:

fitting the pin through the aligned first and second anode sheet bores; and axially compressing the pin length to substantially the anode layer bore length and laterally expanding the pin against the valve metal of the first and second anode sheets.

27. The method of claim 26, wherein the pin and the aligned first and second anode sheet bores are substantially circular.

28. The method of claim 26, wherein the pin and the aligned first and second anode sheet bores are non-circular.

29. The method of claim 21, wherein the expansion riveting step further comprises:

providing a plurality of malleable pellets shaped to fit into the aligned first and second anode sheet bores;

fitting the plurality of malleable pellets into the aligned first and second anode sheet bores; and axially compressing and laterally expanding the plurality of malleable pellets against the valve metal of the first and second anode sheets.

30. The method of claim 21, wherein the aligned first and second anode sheet bores have an anode layer bore length and the expansion rivetng step further comprises:

providing a plurality of malleable pellets shaped to fit into the aligned first and second anode sheet bores;

stacking the plurality of malleable pellets into the aligned first and second anode sheet bores to a pellet stack length that exceeds the anode is layer bore length; and axially compressing the pellet stack length to substantially the anode layer bore length and laterally expanding the pellets against the valve metal of the first and second anode sheets.

31. The method of claim 30, wherein the aligned first and second anode sheet bores are substantially circular.

32. The method of claim 30, wherein the aligned first and second anode sheet bores are non-circular.

33. The method of claim 30, wherein the aligned first and second anode sheet bores are substantially circular and the malleable pellets are substantially cylindrical or spherical.

34. A method of forming an electrode stack assembly of an electrolytic capacitor comprising:

forming an anode layer by:

providing first and second anode sheets fabricated of a valve metal having first and second etched and anodized sheet sides bounded by a sheet edge boring a plurality of first anode sheet bores through the first anode sheet from the first sheet side to the second sheet side;

boring a plurality of second anode sheet bores through the second anode sheet from the first sheet side to the second sheet side; and expansion riveting a plurality of malleable conductive members within the plurality of aligned first and second anode sheet bores into physical and electrical contact with the valve metals of the first and second anode sheets;

providing a cathode layer; and interposing a separator between the anode layer and the cathode layer, the separator carrying an electrolyte.

35. The method of claim 34, wherein the step of forming an anode layer further comprises:

providing a further second anode sheet;

boring a plurality of second anode sheet bores through the further second anode sheet from the first sheet side to the second sheet side;

fitting the second anode sheet against the first sheet side of the first anode sheet and the further second anode sheet against the second sheet side of the first anode sheet, whereby all of the first and second anode sheet bores are axially aligned; and expansion riveting a plurality of malleable conductive members within the aligned first anode sheet bore and second anode sheet bores to the first and second anode sheets.

36. The method of claim 35, further comprising the steps of:

providing the first anode sheet with a notch extending into the first anode sheet edge; providing an anode tab having a first tab portion shaped to fit Into the notch and a second tab portion outwardly extending from the first anode sheet edge and an anode tab bore extending through the first tab portion;

boring second anode sheet bores through the second anode sheets at locations adapted to be aligned with the anode tab bore;

positioning the first tab portion of the anode tab within the notch to substantially align the second anode sheet bores and the anode tab bore; and expansion riveting a second malleable conductive member within the aligned second anode sheet bores and the anode tab bore, whereby the anode tab is physically and electrically coupled to the valve metal of the second anode sheets.

37. A method of forming an electrode stack assembly of an electrolytic capacitor comprising:

forming a plurality of anode layers by, for each anode layer:
- providing first and second anode sheets fabricated of a valve metal having first and second etched and anodized sheet sides bounded by a sheet edge
- boring a first anode sheet bore through the first anode sheet from the first sheet side to the second sheet side;
- boring a second anode sheet bore through the second anode sheet from the first sheet side to the second sheet side; and
- expansion riveting a malleable conductive member within the first and second anode sheet bores into physical and electrical contact with the valve metals of the first and second anode sheets;

providing a plurality of cathode layers; and interposing a separator between each anode layer and each cathode layer, the separator carrying an electrolyte.

38. The method of claim 37, wherein the step of forming a plurality of anode layers further comprises, for each anode layer:
- providing a further second anode sheet;
- boring a second anode sheet bore through the further second anode sheet from the first sheet side to the second sheet side;
- fitting the second anode sheet against the first sheet side of the first anode sheet and the further second anode sheet against the second sheet side of the first anode sheet, whereby all of the first and second anode sheet bores are axially aligned; and
- expansion riveting the malleable conductive member within the aligned first anode sheet bore and second anode sheet bores to the first and second anode sheets.

39. The method of claim 38, wherein the step of forming a plurality of anode layers further comprises, for each anode layer:
- boring a plurality of first anode sheet bores extending through the valve metal of the first anode sheet from the first sheet side to the second sheet side;
- boring a plurality of second anode sheet bores extending through the valve metal of the second anode sheet from the first sheet side to the second sheet side; and
- expansion riveting a plurality of malleable conductive members within the first and second anode sheet bores into physical and electrical contact with the valve metals of the first and second anode sheets.

40. The method of claim 39, further comprising the steps of:
- providing the first anode sheet with a notch extending into the first anode sheet edge;
- providing an anode tab having a first tab portion shaped to fit into the notch and a second tab portion outwardly extending from the first anode sheet edge and an anode tab bore extending through the first tab portion;
- boring second anode sheet bores through the second anode sheets at locations adapted to be aligned with the anode tab bore;
- positioning the first tab portion of the anode tab within the notch to substantially align the second anode sheet bores and the anode tab bore; and
- expansion riveting a second malleable conductive member within the aligned second anode sheet bores and the anode tab bore, whereby the anode tab is physically and electrically coupled to the valve metal of the second anode sheets.

* * * * *

UNITED STATES PATENT AND TRADEMARK OFFICE
CERTIFICATE OF CORRECTION

PATENT NO.    : 6,836,683 B2
DATED         : December 28, 2004
INVENTOR(S)   : Nielsen et al.

It is certified that error appears in the above-identified patent and that said Letters Patent is hereby corrected as shown below:

Column 22,
Line 50, delete "Into" and insert -- into --.

Column 26,
Line 3, delete "anode is layer" and insert -- anode layer --.
Line 55, delete "fit Into" and insert -- fit into --.

Signed and Sealed this

Twenty-fourth Day of May, 2005

JON W. DUDAS
*Director of the United States Patent and Trademark Office*